US009006181B2

(12) United States Patent
Arimura et al.

(10) Patent No.: US 9,006,181 B2
(45) Date of Patent: Apr. 14, 2015

(54) TREATMENT OF RENAL DYSFUNCTION AND MULTIPLE MYELOMA USING PACAP COMPOUNDS

(75) Inventors: Akira Arimura, New Orleans, LA (US); Min Li, Gretna, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 2451 days.

(21) Appl. No.: 11/632,734

(22) PCT Filed: Jul. 21, 2005

(86) PCT No.: PCT/US2005/025836
§ 371 (c)(1),
(2), (4) Date: Aug. 10, 2011

(87) PCT Pub. No.: WO2006/012394
PCT Pub. Date: Feb. 2, 2006

(65) Prior Publication Data
US 2011/0288015 A1    Nov. 24, 2011

Related U.S. Application Data

(60) Provisional application No. 60/589,674, filed on Jul. 21, 2004.

(51) Int. Cl.
*A61K 38/00* (2006.01)
*A61P 13/12* (2006.01)
*A61K 38/08* (2006.01)
*C07K 14/575* (2006.01)

(52) U.S. Cl.
CPC ........... *C07K 14/57563* (2013.01); *A61K 38/00* (2013.01)

(58) Field of Classification Search
CPC .. A61K 38/00; C12N 15/111; C12N 2310/14; C12N 2310/10; C12N 2310/11
See application file for complete search history.

(56) References Cited

U.S. PATENT DOCUMENTS

| | | | |
|---|---|---|---|
| 4,526,938 | A | 7/1985 | Churchill et al. |
| 4,980,286 | A | 12/1990 | Morgan et al. |
| 5,128,242 | A | 7/1992 | Arimura et al. |
| 5,128,326 | A | 7/1992 | Balazs et al. |
| 5,198,542 | A | 3/1993 | Onda et al. |
| 5,436,146 | A | 7/1995 | Shenk et al. |
| 5,679,377 | A | 10/1997 | Bernstein et al. |
| 5,708,022 | A | 1/1998 | Bastos et al. |
| 5,912,015 | A | 6/1999 | Bernstein et al. |
| 5,916,597 | A | 6/1999 | Lee et al. |
| 5,989,463 | A | 11/1999 | Tracy et al. |
| 6,242,563 | B1 | 6/2001 | Dong |
| 6,680,295 | B1 | 1/2004 | Arimura |
| 6,855,308 | B2 | 2/2005 | Thakur |
| 2004/0038888 | A1 | 2/2004 | Mercer et al. |
| 2008/0108573 | A1 | 5/2008 | Duggan |
| 2008/0227954 | A1 | 9/2008 | Larsen |
| 2008/0312157 | A1 | 12/2008 | Levy et al. |

FOREIGN PATENT DOCUMENTS

| | | | | |
|---|---|---|---|---|
| EP | 0 467 279 A2 | * | 1/1992 | ............... C07K 7/10 |
| JP | 2005538942 A | | 12/2005 | |
| JP | 2008501723 A | | 1/2008 | |
| JP | 2008507540 A | | 3/2008 | |
| WO | WO-91/05548 A1 | | 5/1991 | |
| WO | WO-92/06180 A1 | | 4/1992 | |
| WO | WO-92/22635 A1 | | 12/1992 | |
| WO | WO-93/14188 A1 | | 7/1993 | |
| WO | WO-93/20221 A1 | | 10/1993 | |
| WO | WO-94/12649 A2 | | 6/1994 | |
| WO | WO-96/09064 A1 | | 3/1996 | |
| WO | WO-96/20698 A2 | | 7/1996 | |
| WO | WO-99/15154 A1 | | 4/1999 | |
| WO | WO-99/20253 A1 | | 4/1999 | |
| WO | WO-03/092716 A2 | | 11/2003 | |
| WO | WO-2005/120545 A1 | | 12/2005 | |
| WO | WO2006/012394 | | 2/2006 | |
| WO | WO-2007/021498 A1 | | 2/2007 | |
| WO | WO-2009/033767 A2 | | 3/2009 | |

(Continued)

OTHER PUBLICATIONS

Perez-Diaz et al. Multiple myeloma as a treatable cause of stroke: clinical case and review of the literature. Neurologia, 2007. vol. 22, No. 1, pp. 54-57.*
Spandou et al. Erythropoietin attenuates renal injury in experimental acute renal failure ischaemic/reperfusion model. Nephrol Dial Transplant. 2006, vol. 21, pp. 330-336.*
NF-kB in Renal Inflammation. J Am Soc Nephrol, 2010. vol. 21, pp. 1254-1262.*
Arimura et al., 1992, "Pituitary adenylate cyclase activating polypeptide (PACAP): discovery and current status of research." Regul. Pept. 37:287-303.
Arimura et al., 1992, "Receptors for pituitary adenylate cyclase-activating polypeptide: Comparison with vasoactive intestinal peptide receptors." Trends Endocrin. Metab 3:288-294.

(Continued)

*Primary Examiner* — Marcela M Cordero Garcia
(74) *Attorney, Agent, or Firm* — Clark & Elbing LLP; Paul T. Clark, Esq.; Todd Armstrong

(57) ABSTRACT

The present invention relates to methods and compositions for the treatment, management, or prevention of multiple myeloma and/or renal dysfunction in mammals. The methods of the invention comprise the administration of an effective amount of one or more pituitary adenylate cyclase activating polypeptide ("PACAP") compounds, which includes PACAP, vasoactive intestinal peptide ("VIP"), their agonists, analogs, fragments, or derivatives, having one or more PACAP activities. The invention also provides pharmaceutical compositions comprising one or more PACAP compounds of the invention either alone or in combination with one or more other prophylactic/therapeutic agents useful in therapy for the treatment, management, or prevention of multiple myeloma and/or renal dysfunction.

32 Claims, 12 Drawing Sheets

(56) References Cited

FOREIGN PATENT DOCUMENTS

Figure 2:
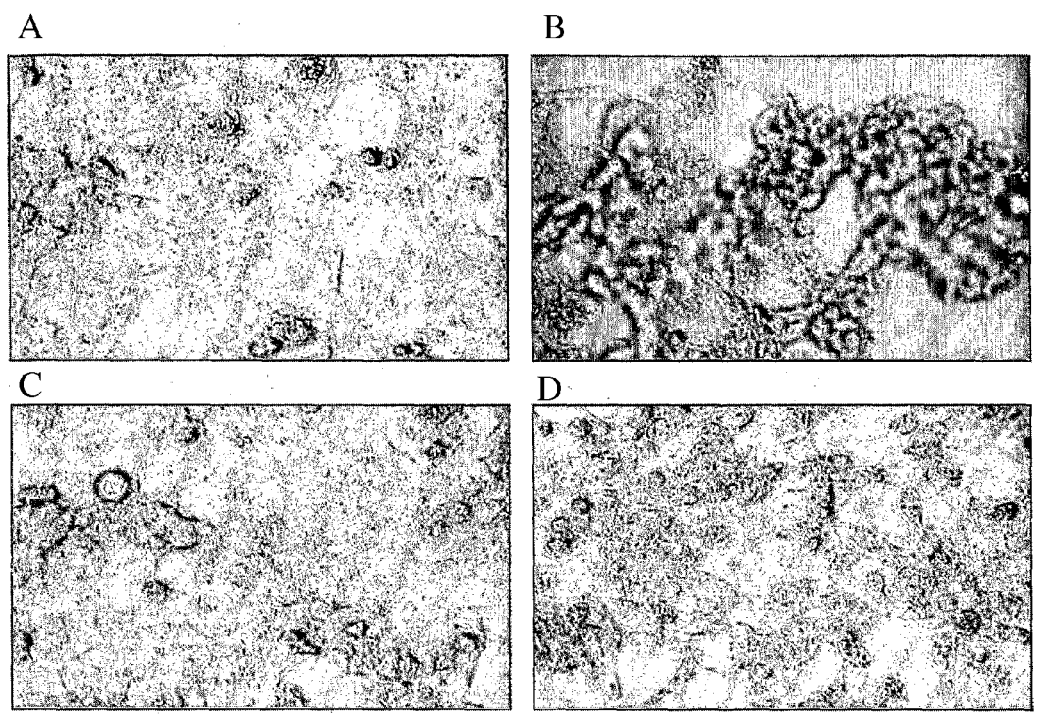

| WO | WO-2011/054001 A2 | 5/2011 |
|---|---|---|
| WO | WO-2011/097581 A2 | 8/2011 |

OTHER PUBLICATIONS

Brenner et al., 1988, "Glomeruli and blood pressure. Less of one, more the other?" Am. J. Hypertens 1:(4 pt 1):335-337.
Decourt et al., 1998, "Complete primary sequences of two lambda immunoglobulin light chains in myelomas with nonamyloid (Randall-type) light chain deposition disease." Am. J. Path. 153:313-318.
Gottschall et al., 1990, "Characterization and distribution of binding sites for the hypothalamic peptide, pituitary adenylate cyclase-activating polypeptide." Endocrin. 127:272-277.
Kitada et al., 1991, "Synthesis and structure-activity relationships of PACAP." Pep. Chem. 1990:239.
Kucher et al., 2005, "Histopathologic comparison of nephrogenic fibrosing dermopathy and scleromyxedema." J. Cutan Path. 32(7): 484-90.
Miyata et al., 1989, "Isolation of a novel 38 residue-hypothalamic polypeptide which stimulates adenylate cyclase in pituitary cells." Biochem Biophys Res. Commun. 164:567-574.
Miyata et al., 1990, "Isolation of a neuropeptide corresponding to the N-terminal 27 residues of the pituitary adenylate cyclase activating polypeptide with 38 residues (PACAP38)." Biochem. Biophys. Res. Commun. 170:643-8.
Ogi et al., 1993, "Molecular cloning and functional expression of a cDNA encoding a human pituitary adenylate cyclase activating polypeptide receptor." Biochem. Biophys. Res. Commun. 196:1511-1521.
Okazaki et al., 1992, "Expression of human pituitary adenylate cyclase activating polypeptide (PACAP) cDNA in CHO cells and characterization of the products." FEBS Lett. 298:49-56.
PCT International Search Report dated Jan. 4, 2006, Int. Appl. No. PCT/US2005/25836.
Sakiyama et al., 1991, "Structure-activity relationship of pituitary adenylate cyclase activating polypeptide (PACAP)" Pep. Chem. 1991:215-220.
Shivers et al., 1991, "Two high affinity binding sites for pituitary adenylate cyclase-activating polypeptide have different tissue distributions" Endocrin. 128:3055-3065.
Sreedharan et al., 1995, "Structure, expression, and chromosomal localization of the type I human vasoactive intestinal peptide receptor gene." Proc. Natl. Acad Sci. USA 92: 2939-2943.
Svoboda et al., 1994, "Molecular cloning and functional characterization of a human VIP receptor from SUP-T1 lymphoblasts." Biochem. Biophys. Res. Commun. 205:1617-1624.
Uchida et al., 1994, "Cytoprotective action of pituitary adenylate cyclase activating polypeptide (PACAP) in ischemia-induced neuronal cell death in rat hippocampus" Soc. Neurosei. vol. 20: Abs. 193.10.
Alessandrini, "Experimental researches on heart and lung preservation," Acta Biomed Ateneo Parmense. 65(3-4):59-73 (Abstract only) (1994).
Atlasz et al., "Extent of retinal damage in carotid artery occlusion-induced hypoperfusion model in PACAP-deficient mice," J Mol Neurosci. 42:266-318 (Abstract only) (2010).
Azuma et al., "PACAP protects mice with dextran sodium sulfate-induced acute colitis," J Mol Neurosci. 42:266-318 (Abstract only) (2010).
Azuma et al., "Regulation of somatolactin release from cultured goldfish pituitary cells by PACAP and MCH," J Mol Neurosci. 42:266-318 (Abstract only) (2010).
Barnes et al., "Glucocorticoid resistance in inflammatory diseases," Lancet. 373(9678):1905-1917 (2009).
Berendsen, "A glimpse of the Holy Grail?," Science. 282(5389):642-3 (1998).
Botia et al., "Neuroprotective effects of PACAP against alcohol toxicity in the developing rat cerebellum," J Mol Neurosci. 42:266-318 (Abstract only) (2010).
Boudard et al., "Inhibition of mouse T-cell proliferation by CGRP and VIP: effects of these neuropeptides on IL-2 production and cAMP synthesis," J Neurosci Res. 29(1):29-41 (1991).
Bradley et al., "Limits of cooperativity in a structurally modular protein: response of the Notch ankyrin domain to analogous alanine substitutions in each repeat," J Mol Biol. 324(2):737-86 (2002).
Buscail et al., "Stimulation of rat pancreatic tumoral AR4-2J cell proliferation by pituitary adenylate cyclase-activating peptide," Gastroenterology. 103(3):1002-1008 (1992).
Campana et al., "Double and triple staining methods for studying the proliferative activity of human B and T lymphoid cells," J Immunol Methods. 107(1):79-88 (1988).
Castorina et al., "PACAP and VIP prevent apoptosis in schwannoma cells," Brain Res. 1241:29-35 (2008).
Cederbaum et al., "Role of oxidative stress in alcohol-induced liver injury," Arch Toxicol. 83(6):519-548 (2009).
Chandler, "Possible mechanisms of bleomycin-induced fibrosis," Clin Chest Med. 11(1):21-30 (1990).
Chang, "Experimental study of the effects of pituitary adenylate cyclase-activating polypeptide (PACAP) and its mechanism on the vascular cell components—the possible relationship between PACAP and atherosclerosis," Sheng Li Ke Xue Jin Zhan. 28:132-135 (Abstract only ) (1997).
Chen et al., "Effects of ectopic overexpression of p21(WAF1/CIP1) on aneuploidy and the malignant phenotype of human brain tumor cells," Oncogene. 13(7):1395-1403 (1996).
Chiodera et al., "Effects of intravenously infused pituitary adenylate cyclase-activating polypeptide on adenohypophyseal Hormone secretion in normal men," Neuroendocrinology. 64(3):242-246 (1996).
Cleek et al., "Biodegradable polymeric carriers for bFGF antibody for cardiovascular application," Pro Intl Symp Control Rel Bioact Mater. 24:853-854 (1997).
Cotten et al., "Receptor-mediated transport of DNA into eukaryotic cells," Methods Enzymol. 217:618-644 (1993).
David et al., Society for Neuroscience (33rd Annual Meeting), New Orleans, Louisiana, #38.1 (2003) (Abstract).
Dejda et al., "Involvement of stathmin 1 in the neurotrophic effects of PACAP in PC12 cells," J Mol Neurosci. 42:266-318 (Abstract only) (2010).
Doan et al., "Design of PAC1/VPAC1 selective analogs as multifunctional drug candidates for the treatment of Parkinson's disease," *J. of Peptide Science*. 16(S1): 153-154, 2010.
Eiden et al., "Signaling pathways involved in PACAP and cytokine interactions regulating adrenomedullary neuropeptide biosynthesis," J Mol Neurosci. 42:266-318 (Abstract only) (2010).
Fukuchi et al., "Pituitary adenylate cyclase-activating polypeptide (PACAP) induces activity-dependent gene expression through the potentiation of N-methyl-$_D$-asparate receptor (NMDA-R) in neurons," J Mol Neurosci. 42:266-318 (Abstract only) (2010).
Fukuchi et al., "Pituitary adenylate cyclase-activating polypeptide (PACAP) induces activity-dependent gene expressions in neurons," J Mol Neurosci. 42:266-318 (Abstract only) (2010).
Girard et al., "Expression and regulation of PACAP/VIP and receptors in micturition reflex pathways of nerve growth factor (NGF) overexpressing (OE) mice," J Mol Neurosci. 42:266-318 (Abstract only) (2010).
Girard et al., "Presence of VIP, PACAP, and their receptors in control and explants cultured mouse major pelvic ganglia," J Mol Neurosci. 42:266-318 (Abstract only) (2010).
Goldspiel et al., "Human gene therapy," Clin Pharm. 12(7):488-505 (1993).
Hammack et al., "Pituitary adenylate cyclase-activating peptide (PACAP) expression and signaling in the bed nucleus of the stria terminalis (BNST) mediate increased anxiety-like behavior following chronic variate stress," J Mol Neurosci. 42:266-318 (Abstract only) (2010).

(56) References Cited

OTHER PUBLICATIONS

Hatanaka et al., "Identification of a novel-signaling cascade specifically involved in the light-induced phase advance of circadian rhythm by using PACAP knockout mice," J Mol Neurosci. 42:266-318 (Abstract only) (2010).
Hayata et al., "PACAP plays a crucial role in the stress-induced activation of HPA-axis ," J Mol Neurosci. 42:266-318 (Abstract only) (2010).
Holst et al., "Increased plasma levels of vasoactive intestinal polypeptide in pre-eclampsia," Br J Obstet Gynaecol. 98(8):803-806 (1991).
Horvath et al., "The role of endogenous PACAP in protection against hypoxia and oxidative stress: in vitro studies in PACAP knockout mice," J Mol Neurosci. 42:266-318 (Abstract only) (2010).
Hoshino et al., "S-phase fraction of human brain tumors in situ measured by uptake of bromodeoxyuridine," Int J Cancer. 38(3): 369-374 (1986).
Ikeda et al., "Involvement of pituitary adenylate cyclase-activating polypeptide (PACAP) in diabetic neuropathy of streptozotocin (STZ) treated mice," J Mol Neurosci. 42:266-318 (Abstract only) (2010).
Ishido, "Temporal dynamics of gene expression during PACAP-induced PC12 cell differentiation," J Mol Neurosci. 42:266-318 (Abstract only) (2010).
Ishihama et al., "Effects of environmental factors during development on abnormal phenotypes in PACAP knock-out mice," J Mol Neurosci. 42:266-318 (Abstract only) (2010).
Jeoung et al., "Effects of tumor necrosis factor-alpha on antimitogenicity and cell cycle-related proteins in MCF-7 cells," J Biol Chem. 270(31):18367-18373 (1995).
Juarranz et al., "Vasoactive intestinal peptide (VIP) stimulates rat prostatic epithelial cell proliferation," Prostate. 47(4):285-292 (2001).
Kawano et al., "Autocrine generation and requirement of BSF-2/IL-6 for human multiple myelomas," Nature. 332(6159):83-85 (1988).
Kiem et al., "Retrovirus-mediated gene transduction into canine peripheral blood repopulating cells," Blood. 83(6): 1467-1473 (1994).
Le et al., "PAC1 and PACAP expression, signaling, and effect on the growth of HCT8, human colonic tumor cells," Regul Pept. 109(1-3):115-125 (2002).
Leister et al., "Vasoactive intestinal polypeptide and gastrin-releasing peptide attenuate hepatic microvasculatory disturbances following intestinal ischemia and reperfusion," Digestion. 66(3):186-192 (2002).
Li et al., "Prohormone convertases 1 and 2 process ProPACAP and generate matured, bioactive PACAP38 and PACAP27 in transfected rat pituitary GH4C1 cells," Neuroendocinology. 69(3):217-226 (1999).
Li et al., "Signaling cascades involved in neuroprotection by subpicomolar pituitary adenylate cyclase-activating polypeptide 38," J Mol Neurosci. 27(1):91-105 (2005).
Li et al., "Subcellular distribution of p21 and PCNA in normal and repair-deficient cells following DNA damage" Curr Biol. 6(2):189-199 (1996).
Luo et al., "Vasoactive intestinal peptide attenuates concanavalin A-mediated liver injury," Eur J Pharmacol. 607(1-3):226-233 (2009).
Maderdrut et al., "Pituitary adenylate cyclase-activating polypeptide (PACAP) analogs increase the therapeutic index of anticancer agents for blood cancers," J Mol Neurosci. 42:266-318 (Abstract only) (2010).
Miura et al., "Regulatory mechanism of PAC1 gene expression by nerve growth factor (NGF) in PC12 cells," J Mol Neurosci. 42:266-318 (Abstract only) (2010).
Molnar et al., "The role of the circulatory system in the transportation of PACAP-like compounds in earthworms," J Mol Neurosci. 42:266-318 (Abstract only) (2010).
Nakagawa et al., "Pituitary adenylate cyclase activating polypeptide (PACAP) enhances blood-brain barrier (BBB) functions of rat brain microvascular endothelial cells in vitro," J Mol Neurosci. 42:266-318 (Abstract only) (2010).
Nakata et al., "Intra-islet PACAP protects pancreatic beta-cells against glucotoxicity and lipotoxicity," J Mol Neurosci. 42:266-318 (Abstract only) (2010).
Ng et al., "Molecular cloning and characterization of a VPAC receptor in the inshore hagfish, *Eptatretus burgeri*," J Mol Neurosci. 42:266-318 (Abstract only) (2010).
Ngo et al., "Computational complexity, protein structure prediction, and the levinthal paradox," Birkhäuser Boston. 491-491 (1994).
Pirger et al., "Memory, cAMP, and PACAP—a phylogenetically conserved function? Studies in Lymnea stagnalis ," J Mol Neurosci. 42:266-318 (Abstract only) (2010).
Racz et al., "Effects of PACAP on mitochondrial antiapoptotic pathways and cytokine expression in rates subjected to renal ischemia/reperfusion," J Mol Neurosci. 42:266-318 (Abstract only) (2010).
Rácz et al., "Protective effects of pituitary adenylate cyclase activating polypeptide in endothelial cells against oxidative stress-induced apoptosis," Gen Comp Endocrinol. 153:115-123 (2007).
Rafferty et al., "Rescue of functional F508del cystic fibrosis transmembrane conductance regulator by vasoactive intestinal peptide in the human nasal epithelial cell line JME/CF15," J Pharmacol Exp Ther. 331(1):2-13 (2009).
Raoult et al., "Tissue-type plasminogen activator (tPA) as a PACAP-regulated gene in neuronal cells," J Mol Neurosci. 42:266-318 (Abstract only) (2010).
Robberecht et al., "Structural requirements for the occupancy of pituitary adenylate-cyclase-activating-peptide (PACAP) receptors and adenylate cyclase activation in human neuroblastoma NB-OK-1 cell membranes. Discovery of PACAP(6-38) as a potent antagonist," Eur J Biockem. 207(1):239-46 (1992).
Rudinger, "Characteristics of the amino acids as components of a peptide hormone sequence," JA Parsons, Ed. 1-7 (1976).
Sakurai et al., "The roles of pancreatic PACAP in cerulein-inducded pancreatitis," J Mol Neurosci. 42:266-318 (Abstract only) (2010).
Sandor et al., "Impaired nocifensive behaviors and mechanical hyperalgesia, but enhanced thermal hyperaglesia in PCAP knockout mice," J Mol Neurosci. 42:266-318 (Abstract only) (2010).
Sato et al., "Suppression of oxidative stress by PACAP," J Mol Neurosci. 42:266-318 (Abstract only) (2010).
Shibata et al., "15-Deoxy-Δ-prostaglandin $J_2$ enhances NGF-induced neurite outgrowth in PC12 cells via a CRTH2 receptor-p38 MAP kinase pathway," J Mol Neurosci. 42:266-318 (Abstract only) (2010).
Shivers et al., "Two high affinity binding sites for pituitary adenylate cyclase-activating polypeptide have different tissue distributions," Endocrinology. 128(6): 3055-65 (1991).
Sigma, "Designing custom peptides,"<http://www.sigma-genosys.com/peptide_design.asp>, retrieved on Dec. 16, 2004 (2 pages).
Sugawara et al., "The alternative regulation of pituitary adenylate cyclase-activating polylpeptide (PACAP) gene expression by neural-restrictive silencer," J Mol Neurosci. 42:266-318 (Abstract only) (2010).
Szabadfi et al., "Effects of PACAP in streptozotocin-induced rat model of diabetic retinophathy," J Mol Neurosci. 42:266-318 (Abstract only) (2010).
Szakaly et al., "The in vivo role of endogenous PACAP kidney ischemia/reperfusion: studies with knockout mice and radioimmunoassay," J Mol Neurosci. 42:266-318 (Abstract only) (2010).
Tatsuno et al., "Inhibition of mitogen-stimulated proliferation of murine splenocytes by a novel neuropeptide, pituitary adenylate cyclase activating polypeptide: a comparative study with vasoactive intestinal peptide," Endocrinology. 128(2):728-734 (1991).
Tominaga et al., "The cell specific promoter in upstream region of human PACAP testis-specific exon," J Mol Neurosci. 42:266-318 (Abstract only) (2010).
Valiante et al., "Localization of pituitary adenylate cyclase-activating polypeptide (PACAP) receptors in peripheral tissues during mouse perinatal development," J Mol Neurosci. 42:266-318 (Abstract only) (2010).
Valiante et al., "Pituitary adenylate cyclase-activating polypeptide and its receptors in diet-induced obese rat adrenal glands," J Mol Neurosci. 42:266-318 (Abstract only) (2010).
Voet et al., "Abonormal Hemoglobins," John Wiley & Sons Inc., 235-241 (1995).

(56) References Cited

OTHER PUBLICATIONS

Watanabe et al., "PACAP stimulates catecholamine release from adrenal medulla: a novel noncholinergic secretagogue," Am J Physiol. 269(5 Pt 1):E903-E909 (1995).
Yamada et al., "Increased stathmin 1 expression in the dentate gyrus causes abnormal axonal arborizations potential relevance to schizophrenia," J Mol Neurosci. 42:266-318 (Abstract only) (2010).
Yang et al., "The activation of PACAP receptor (PAC1 receptor) differentially targets NR2A containing NMDA receptors and favors LTP induction," J Mol Neurosci. 42:266-318 (Abstract only) (2010).
Extended European Search Report for European Patent Application No. 11740499.6, dated Sep. 13, 2013 (5 pages).
English Translation of the Notification of the Second Office Action for Chinese Patent Application No. 200980145368.4, mailed Apr. 18, 2013 (7 pages).
International Search Report for International Application No. PCT/US2005/25836, mailed Jan. 4, 2006 (1 page).
Allam, "Vasoactive intestinal peptide inhibits liver pathology in acute murine *Schistosomiasis mansoni* and modulates IL-10, IL-12 and TNF-alpha production," Immunobiology. 212(8):603-612 (2007).
Altschul et al., "Basic local alignment search tool," J Mol Biol. 215(3):403-410 (1990).
Altschul et al., "Gapped BLAST and PSI-BLAST: a new generation of protein database search programs," Nucleic Acids Res. 25(17):3389-3402 (1997).
Ameen et al., "CFTR channel insertion to the apical surface in rat duodenal villus epithelial cells is upregulated by VIP in vivo," J Cell Sci. 112:887-894 (1999).
Arimura, "PACAP functions as a neurotrophic factor," Ann NY Acad Sci. 739:228-243 (1994).
Arimura, "Perspectives on pituitary adenylate cyclase activating polypeptide (PACAP) in the neuroendocrine, endocrine, and nervous systems," Jpn J Physiol. 48(5):301-331 (1998).
Bacus et al., "Biological grading of breast cancer using antibodies to proliferating cells and other markers," Am J Pathol. 135(5):783-792 (1989).
Banks et al., "Passage of pituitary adenylate cyclase activating polypeptide1-27 and pituitary adenylate cyclase activating polypeptide1-38 across the blood-brain barrier," J Pharmacol Exp Ther. 267(2):690-696 (1993).
Boesen et al., "Circumvention of chemotherapy-induced myelosuppression by transfer of the mdr1 gene," Biotherapy. 6:291-302 (1994).
Brenneman et al., "Chemokine release is associated with the protective action of PACAP-38 against HIV envelope protein neurotoxicity," Neuropeptides. 36(4):271-280 (2002).
Buchwald et al., "Long-term, continuous intravenous heparin administration by an implantable infusion pump in ambulatory patients with recurrent venous thrombosis," Surgery. 88(4):507-516 (1980).
Ceponis et al. "Epithelial cell signaling responses to enterohemorrhagic *Escherichia coli* infection," Mem Inst Oswaldo Cruz. 100(Suppl 1):199-203 (2005).
Clowes et al., "Long-term biological response of injured rat carotid artery seeded with smooth muscle cells expressing retrovirally introduced human genes," J Clin Invest. 93(2):644-651 (1994).
Delgado et al., "Vasoactive intestinal peptide and pituitary adenylate cyclase-activating polypeptide inhibit nuclear factor-kB-dependent gene activation at multiple levels in the human monocytic cell line THP-1," J Biol Chem. 276(1):369-380 (2001).
Doberer et al., "Pulmonary and systemic effects of inhaled PACAP38 in healthy male subjects," Eur J Clin Invest. 37(8):665-672 (2007).
Dufes et al., "Effects of the vasoactive intestinal peptide (VIP) and related peptides on glioblastoma cell growth in vitro" J Mol Neurosci. 21(2):91-102 (2003).
During et al., Controlled release of dopamine from a polymeric brain implant: in vivo characterization, Ann Neurol. 25(4):351-356 (1989).
Dérand et al., "Activation of VPAC1 receptors by VIP and PACAP-27 in human bronchial epithelial cells induces CFTR-dependent chloride secretion," Br J Pharmacol. 141(4):698-708 (2004).

Ferencz et al., "Influence of PACAP on oxidative stress and tissue injury following small-bowel autotransplantation," J Mol Neurosci. 37(2):168-176 (2009).
Figiel et al., "Pituitary adenylate cyclase-activating polypeptide (PACAP), a neuron-derived peptide regulating glial glutamate transport and metabolism," J Neurosci. 20(10):3596-3605 (2000).
Filipsson et al. "Pituitary adenylate cyclase-activating polypeptide stimulates insulin and glucagon secretion in humans," J Clin Endocrinol Metab. 82(9):3093-3098 (1997).
Ganea et al., "Vasoactive intestinal peptide (VIP) and pituitary adenylate cyclase-activating polypeptide (PACAP) as modulators of both innate and adaptive immunity," Crit Rev Oral Biol Med. 13(3):229-237 (2002).
Gasz et al., "Pituitary adenylate cyclase activating polypeptide protects cardiomyocytes against oxidative stress-induced apoptosis," Peptides. 27(1):87-94 (2006).
Greenstein et al., "Characterization of the MM.1 human multiple myeloma (MM) cell lines: a model system to elucidate the characteristics, behavior, and signaling of steroid-sensitive and -resistant MM cells," Exp Hematol. 31(4):271-282 (2003).
Grossman et al., "Retroviruses: delivery vehicle to the liver," Curr Opin Genet Dev. 3(1):110-114 (1993).
Gupta, "Intrinsic multidrug resistance phenotype of Chinese hamster (rodent) cells in comparison to human cells," Biochem Biophys Res Commun. 153(2):598-605 (1988).
Gutiérrez-Cañas et al., "VIP and PACAP are autocrine factors that protect the androgen-independent prostate cancer cell line PC-3 from apoptosis induced by serum withdrawal," Br J Pharmacol. 139(5):1050-1058 (2003).
Haberlet et al., "Vasoactive intestinal peptide gene alterations in patients with idiopathic pulmonary arterial hypertension," Eur J Hum Genet. 15(1):18-22 (2007).
Harper et al., "The p21 Cdk-interacting protein Cip1 is a potent inhibitor of G1 cyclin-dependent kinases," Cell. 75(4):805-816 (1993).
Hawke et al., "PACAP neurons in the hypothalamic ventromedial nucleus are targets of central leptin signaling," J Neurosci. 29(47):14828-14835 (2009).
Hayez et al., "The neuropeptides vasoactive intestinal peptide (VIP) and pituitary adenylate cyclase activating polypeptide (PACAP) modulate several biochemical pathways in human leukemic myeloid cells," J Neuroimmunol. 149(1-2):167-181 (2004).
Hideshima et al., "Targeting p38 MAPK inhibits multiple myeloma cell growth in the bone marrow milieu," Blood. 101(2):703-705 (2003).
Hogle, "Cytoprotective agents used in the treatment of patients with cancer," Semin Oncol Nurs. 23(3):213-224 (2007).
Howard et al., "Intracerebral drug delivery in rats with lesion-induced memory deficits," J Neurosurg. 71(1):105-112 (1989).
Karlin et al., "Applications and statistics for multiple high-scoring segments in molecular sequences," Proc Natl Acad Sci USA. 90(12):5873-5877 (1993).
Karlin et al., "Methods for assessing the statistical significance of molecular sequence features by using general scoring schemes," Proc Natl Acad Sci USA. 87(6):2264-2268 (1990).
Kinhult et al., "Pituitary adenylate cyclase-activating peptide inhibits neutrophil chemotaxis," Peptides. 22(12): 2151-2154 (2001).
Kintzel, "Anticancer drug-induced kidney disorders," Drug Saf. 24(1):19-38 (2001).
Koller et al., "Inactivating the beta 2-microglobulin locus in mouse embryonic stem cells by homologous recombination," Proc Natl Acad Sci USA. 86(22):8932-8935 (1989).
Kong et al., "Reduction of lipopolysaccharide-induced neurotoxicity in mixed cortical neuron/glia cultures by femtomolar concentrations of pituitary adenylate cyclase-activating polypeptide," Neuroscience. 91(2):493-500 (1999).
Kono et al., "Diphenyleneiodonium sulfate, an NADPH oxidase inhibitor, prevents early alcohol-induced liver injury in the rat," Am J Physiol Gastrointest Liver Physiol. 280(5):G1005-G1012 (2001).
Langer, "New methods of drug delivery," Science. 249(4976):1527-1533 (1990).
Lee et al., "Neutrophil activation and production of reactive oxygen species in pre-eclampsia," J Hypertens. 21(2):395-402 (2003).

(56) References Cited

OTHER PUBLICATIONS

Lelièvre et al., "Differential expression and function of PACAP and VIP receptors in four human colonic adenocarcinoma cell lines," Cell Signal. 10(1):13-26 (1998).
Levy et al., "Inhibition of calcification of bioprosthetic heart valves by local controlled-release diphosphonate," Science. 228(4696):190-192 (1985).
Leyton et al., "PACAP(6-38) inhibits the growth of prostate cancer cells," Cancer Lett. 125(1-2):131-139 (1998).
Leyton et al., "PACAP(6-38) is a PACAP receptor antagonist for breast cancer cells," Breast Cancer Res Treat. 56(2):177-186 (1999).
Li et al., "Intravenous infusion of pituitary adenylate cyclase-activating polypeptide (PACAP) in a patient with multiple myeloma and myeloma kidney: a case study," Peptides. 28(9):1891-1895 (2007).
Li et al., "Pituitary adenylate cyclase-activating polypeptide precursor is processed solely by prohormone convertase 4 in the gonads," Endocrinology. 141(10):3723-3730 (2000).
Li et al., "Renoprotection by pituitary adenylate cyclase-activating polypeptide in multiple myeloma and other kidney diseases," Regul Pept. 145(1-3):24-32 (2008).
Martinez et al., "Anti-inflammatory role in septic shock of pituitary adenylate cyclase-activating polypeptide receptor," Proc Natl Aced Sci USA 99(2):1053-1058 (2002).
Mastrangeli et al., "Diversity of airway epithelial cell targets for in vivo recombinant adenovirus-mediated gene transfer" J Clin Invest. 91(1):225-234 (1993).
Matsuda et al., "Regulation of feeding behavior by pituitary adenylate cyclase-activating polypeptide (PACAP) and vasoactive intestinal polypeptide (VIP) in vertebrates," Peptides. 28(9):1761-1766 (2007).
Mounien et al., "Pituitary adenylate cyclase-activating polypeptide inhibits food intake in mice through activation of the hypothalamic melanocortin system," Neuropsychopharmacology. 34(2):424-435 (2009).
Mukohyama et al., "The inhibitory effects of vasoactive intestinal peptide and pituitary adenylate cyclase-activating polypeptide on osteoclast formation are associated with upregulation of osteoprotegerin and downregulation of RANKL and RANK," Biochem Biophys Res Commun. 271(1):158-163 (2000).
Mulligan, "The basic science of gene therapy," Science. 260(5110):926-932 (1993).
Murck et al., "Pituitary adenylate cyclase-activating peptide affects homeostatic sleep regulation in healthy young men," Am J Physiol Endocrinol Metab. 292(3):E853-E857 (2007).
Ning et al., "Intratumoral radioimmunotherapy of a human colon cancer xenograft using a sustained-release gel," Radiother Oncol. 39(2):179-189 (1996).
Oka et al., "Pituitary adenylate cyclase-activating polypeptide inhibits transforming growth factor-beta1-induced apoptosis in a human pituitary adenoma cell line," Am J Pathol. 155(6):1893-1900 (1999).
Onoue et al., "Pituitary adenylate cyclase-activating polypeptide attenuates streptozotocin-induced apoptotic death of RIN-m5F cells through regulation of Bcl-2 family protein mRNA expression," FEBS J. 275(22):5542-5551 (2008).
Ottaway et al., "Interaction of vasoactive intestinal peptide with mouse lymphocytes: specific binding and the modulation of mitogen responses," J Immunol. 132(1):417-423 (1984).
Otto et al., "Pulmonary hypertension and right heart failure in pituitary adenylate cyclase-activating polypeptide type I receptor-deficient mice," Circulation. 110(20):3245-3251 (2004).
Reglodi et al. "Pituitary adenylate cyclase activating polypeptide protects dopaminergic neurons and improves behavioral deficits in a rat model of parkinson's disease," Behav Brain Res. 151(1-2):303-312 (2004).
Reglodi et al., "Delayed systemic administration of PACAP38 is neuroprotective in transient middle cerebral artery occlusion in the rat," Stroke. 31(6):1411-1417 (2000).
Reubi, "Peptide receptors as molecular targets for cancer diagnosis and therapy," Endocr Rev. 24(4):389-427 (2003).

Riera et al., "The enhancement of endogenous cAMP with pituitary adenylate cyclase-activating polypeptide protects rat kidney against ischemia through the modulation of inflammatory response," Transplantation. 72(7):1217-1223 (2001).
Rosenfeld et al., "Adenovirus-mediated transfer of a recombinant alpha 1-antitrypsin gene to the lung epithelium in vivo," Science. 252(5004):431-434 (1991).
Rosenfeld et al., "In vivo transfer of the human cystic fibrosis transmembrane conductance regulator gene to the airway epithelium," Cell. 68(1):143-155 (1992).
Said et al., "Moderate pulmonary arterial hypertension in male mice lacking the vasoactive intestinal peptide gene," Circulation. 115(10):1260-1268 (2007).
Salmons et al., "Targeting of retroviral vectors for gene therapy," Hum Gene Ther. 4(2):129-141, (1993).
Sano et al., "The effect of pituitary adenylate cyclase activating polypeptide on cultured rat cardiocytes as a cardioprotective factor," Regul Pept. 109(1-3):107-113 (2002).
Saudek et al., "A preliminary trial of the programmable implantable medication system for insulin delivery," N Engl J Med. 321(9):574-579 (1989).
Segre et al., "Receptors for secretin, calcitonin, parathyroid hormone (PTH)/PTH-related peptide, vasoactive intestinal peptide, glucagon-like peptide 1, growth hormone-releasing hormone, and glucagon belong to a newly discovered G-protein-linked receptor family," Trends Endocrinol Metab. 4(10):309-314 (1993).
Sergejeva et al., "A synthetic VIP peptide analogue inhibits neutrophil recruitment in rat airways in vivo," Regul Pept. 117(2):149-154 (2004).
Sherwood et al., "The origin and function of the pituitary adenylate cyclase-activating polypeptide (PACAP)/glucagon superfamily," Endocr Rev. 21(6):619-670 (2000).
Steenstrup et al., "Pituitary adenylate cyclase activating polypeptide (PACAP): occurrence and vasodilatory effect in the human uteroplacental unit," Regul Pept. 61(3):197-204 (1996).
Szakaly et al.," Effects of PACAP on survival and renal morphology in rats subjected to renal ischemia/reperfusion," J Mol Neurosci. 36(1-3):89-96 (2008).
Takemura et al., "Doxorubicin-induced cardiomyopathy from the cardiotoxic mechanisms to management," Prog Cardiocasc Dis. 49(5):330-352 (2007).
Thakur et al., "Regulation of macrophage activation in alcoholic liver disease," J Gastroenterol Hepatol. 22(Suppl 1):S53-S56 (2007).
Trejter et al., "Studies on the involvement of endogenous neuropeptides in the control of thymocyte proliferation in the rat," Histol Histopathol. 16(1).155-158 (2001).
Turner et al., "Treatment of human prostate cancer cells with dolastatin 10, a peptide isolated from a marine shell-less mollusc," Prostate. 34(3):175-181 (1998).
Uchida et al., "Prevention of ischemia-induced death of hippocampal neurons by pituitary adenylate cyclase activating polypeptide," Brain Res. 736(1-2):280-286 (1996).
Vassilev et al., "The levels of ubiquitinated histone H2A are highly upregulated in transformed human cells: partial colocalization of uH2A clusters and PCNA/cyclin foci in a fraction of cells in S-phase," J Cell Sci. 108(Pt 3):1205-1215 (1995).
Vaudry et al., "Pituitary adenylate cyclase-activating polypeptide and its receptors: from structure to functions," Pharmacol Rev. 52:269-324 (2000).
Winding et al. "Pituitary adenylyl cyclase-activating polypeptides and vasoactive intestinal peptide inhibit bone resorption by isolated rabbit osteoclasts," Exp Physiol. 82(5):871-886 (1997).
Wu et al., "Comparative analysis of cortical gene expression in mouse models of Alzheimer's disease," Neurobiol Aging. 27(3):377-386 (2006).
Wu et al., "Receptor-mediated in vitro gene transformation by a soluble DNA carrier system," J Biol Chem. 262(10):4429-4432 (1987).
Yang et al., "Pituitary adenylate cyclase-activating polypeptide (PACAP) 38 and PACAP4-6 are neuroprotective through inhibition of NADPH oxidase: potent regulators of microglia-mediated oxidative stress," J Pharmacol Exp Ther. 319(2):595-603 (2006).

(56) References Cited

OTHER PUBLICATIONS

Zabalou et al., "A three-season comparative analysis of the chromosomal distribution of P and hobo mobile elements in a natural population of *Drosophila melanogaster*," Hereditas. 120(2):127-140 (1994).
Zhu et al., "Heteromeric Kv1 potassium channel expression: amino acid determinants involved in processing and trafficking to the cell surface," J Biol Chem. 278(28):25558-25567 (2003).
Zia et al., "Pituitary adenylate cyclase activating peptide receptors regulate the growth of non-small cell lung cancer cells," Cancer Res. 55(21):4886-4891 (1995).
Zijlstra et al., "Germ-line transmission of a disrupted $\beta_2$-microglobulin gene produced by homologous recombination in embryonic stem cells," Nature. 342(6248):435-438 (1989).
English Translation of Final Office Action for Japanese Patent Application No. 2007-522734, dated May 17, 2011 (8 pages).
English Translation of Office Action for Japanese Patent Application No. 2007-522734, dated May 17, 2012 (8 pages).
Extended European Search Report for European Patent Application No. 05791771.8, dated Jun. 5, 2009 (13 pages).
International Preliminary Report on Patentability and Written Opinion of the International Searching Authority for International Application No. PCT/US2005/025836, issued Jan. 27, 2007 (4 pages).
International Preliminary Report on Patentability and Written Opinion of the International Searching Authority for International Application No. PCT/US2009/058445, mailed Apr. 30, 2011 (4 pages).
Office Action for Canadian Patent Application No. 2,574,709, dated Apr. 19, 2012 (6 pages).
Hammack, S.E. *Abstracts*, 9th International Symposium on VIP, PACAP, and Related Peptides, Kagoshima, Japan, Oct. 5-8, 2009; J Mol Neurosci. 42:277 (2010).
Hagino, N. *Abstracts*, 9th International Symposium on VIP, PACAP, and Related Peptides, Kagoshima, Japan, Oct. 5-8, 2009; J Mol Neurosci. 42:277-8 (2010).
Shintani, N. *Abstracts*, 9th International Symposium on VIP, PACAP, and Related Peptides, Kagoshima, Japan, Oct. 5-8, 2009; J Mol Neurosci. 42:278-9 (2010).
Shen, et al. *Abstracts*, 9th International Symposium on VIP, PACAP, and Related Peptides, Kagoshima, Japan, Oct. 5-8, 2009; J Mol Neurosci. 42:280 (2010).
Vallejo, M. *Abstracts*, 9th International Symposium on VIP, PACAP, and Related Peptides, Kagoshima, Japan, Oct. 5-8, 2009; J Mol Neurosci. 42:280 (2010).
Grammas, et al. *Abstracts*, 9th International Symposium on VIP, PACAP, and Related Peptides, Kagoshima, Japan, Oct. 5-8, 2009; J Mol Neurosci. 42:280-1 (2010).
Ohtaki, et al. *Abstracts*, 9th International Symposium on VIP, PACAP, and Related Peptides, Kagoshima, Japan, Oct. 5-8, 2009; J Mol Neurosci. 42:281 (2010).
Nonaka, et al. *Abstracts*, 9th International Symposium on VIP, PACAP, and Related Peptides, Kagoshima, Japan, Oct. 5-8, 2009; J Mol Neurosci. 42:281-2 (2010).
Mori et al., S.E. *Abstracts*, 9th International Symposium on VIP, PACAP, and Related Peptides, Kagoshima, Japan, Oct. 5-8, 2009; J Mol Neurosci. 42:295 (2010).
Kiss, et al. *Abstracts*, 9th International Symposium on VIP, PACAP, and Related Peptides, Kagoshima, Japan, Oct. 5-8, 2009; J Mol Neurosci. 42:282 (2010).
Reglodi, et al. *Abstracts*, 9th International Symposium on VIP, PACAP, and Related Peptides, Kagoshima, Japan, Oct. 5-8, 2009; J Mol Neurosci. 42:282-3 (2010).
Tamas, et al. *Abstracts*, 9th International Symposium on VIP, PACAP, and Related Peptides, Kagoshima, Japan, Oct. 5-8, 2009; J Mol Neurosci. 42:283 (2010).
Valiante, et al. *Abstracts*, 9th International Symposium on VIP, PACAP, and Related Peptides, Kagoshima, Japan, Oct. 5-8, 2009; J Mol Neurosci. 42:283 (2010).
Banks, W.A. *Abstracts*, 9th International Symposium on VIP, PACAP, and Related Peptides, Kagoshima, Japan, Oct. 5-8, 2009; J Mol Neurosci. 42:283-4 (2010).
Nagata, et al. *Abstracts*, 9th International Symposium on VIP, PACAP, and Related Peptides, Kagoshima, Japan, Oct. 5-8, 2009; J Mol Neurosci. 42:285-6 (2010).
Matsuda, et al. *Abstracts*, 9th International Symposium on VIP, PACAP, and Related Peptides, Kagoshima, Japan, Oct. 5-8, 2009; J Mol Neurosci. 42:286 (2010).
Lu, et al. *Abstracts*, 9th International Symposium on VIP, PACAP, and Related Peptides, Kagoshima, Japan, Oct. 5-8, 2009; J Mol Neurosci. 42:286-7 (2010).
Ferencz, et al. *Abstracts*, 9th International Symposium on VIP, PACAP, and Related Peptides, Kagoshima, Japan, Oct. 5-8, 2009; J Mol Neurosci. 42:287 (2010).
Lee, et al. *Abstracts*, 9th International Symposium on VIP, PACAP, and Related Peptides, Kagoshima, Japan, Oct. 5-8, 2009; J Mol Neurosci. 42:289 (2010).
Horvath et al., S.E. *Abstracts*, 9th International Symposium on VIP, PACAP, and Related Peptides, Kagoshima, Japan, Oct. 5-8, 2009; J Mol Neurosci. 42:296 (2010).
Doan, et al. *Abstracts*, 9th International Symposium on VIP, PACAP, and Related Peptides, Kagoshima, Japan, Oct. 5-8, 2009; J Mol Neurosci. 42:289-90 (2010).
Eiden et al., S.E. *Abstracts*, 9th International Symposium on VIP, PACAP, and Related Peptides, Kagoshima, Japan, Oct. 5-8, 2009; J Mol Neurosci. 42:296-297 (2010).
Ushiyama, et al. *Abstracts*, 9th International Symposium on VIP, PACAP, and Related Peptides, Kagoshima, Japan, Oct. 5-8, 2009; J Mol Neurosci. 42:290 (2010).
Lutz et al., S.E. *Abstracts*, 9th International Symposium on VIP, PACAP, and Related Peptides, Kagoshima, Japan, Oct. 5-8, 2009; J Mol Neurosci. 42:297 (2010).
Li, et al. *Abstracts*, 9th International Symposium on VIP, PACAP, and Related Peptides, Kagoshima, Japan, Oct. 5-8, 2009; J Mol Neurosci. 42:291-2 (2010).
Gozes, et al. *Abstracts*, 9th International Symposium on VIP, PACAP, and Related Peptides, Kagoshima, Japan, Oct. 5-8, 2009; J Mol Neurosci. 42:292-3 (2010).
Nakamachi, et al. *Abstracts*, 9th International Symposium on VIP, PACAP, and Related Peptides, Kagoshima, Japan, Oct. 5-8, 2009; J Mol Neurosci. 42:293 (2010).
Tamas, et al. *Abstracts*, 9th International Symposium on VIP, PACAP, and Related Peptides, Kagoshima, Japan, Oct. 5-8, 2009; J Mol Neurosci. 42:293-4 (2010).
Said, S. *Abstracts*, 9th International Symposium on VIP, PACAP, and Related Peptides, Kagoshima, Japan, Oct. 5-8, 2009; J Mol Neurosci. 42:294 (2010).
Bourgault et al., "Novel stable PACAP analogs with potent activity towards the PAC1 receptor," *Peptides*. 29(6):919-32 (2008).
Ferencz et al., "Comparison of intestinal warm ischemic injury on PACAP knock-out and wild-type mice," J Mol Neurosci. 42:266-318 (Abstract only) (2010).
Fukuchi et al., "Pituitary adenylate cyclase-activating polypeptide (PACAP) induces activity-dependent gene expression through the potentiation of N-methyl-D-asparate receptor (NMDA-R) in neurons," J Mol Neurosci. 42:266-318 (Abstract only) (2010).
Hammack, "A role for pituitary adenylate cyclase-activating peptide (PACAP) expression and signaling in the bed nucleus of the stria terminalis (BNST) in stress-induced anxiety-like behavior," J Mol Neurosci. 42:266-318 (Abstract only) (2010).
Hou et al., "Structural requirements for the occupancy of rat brain PACAP receptors and adenylate cyclase activation," Neuropharmacology. 33(10):1189-1195 (1994).
Lerner et al., "Maxadilan, a PAC1 receptor agonist from sand flies," Peptides. 28(9):1651-4 (2007).
Paran et al., "Extensive colonic ischemia following treatment with bevacizumab, fluouracil and CPT-11 in a young patient with advanced adenocarcinoma of the rectum" Isr Med Assoc J. 9(6):488-9 (2007).
Sun et al., "Solution structure and mutational analysis of pituitary adenylate cyclase-activating polypeptide binding to the extracellular domain of PAC1-RS," Proc Natl Acad Sci USA. 104(19):7875-7880 (2007).
English Translation of Office Action for Chinese Patent Application No. 201080060381.2, mailed Jul. 12, 2013 (7 pages).

(56) References Cited

OTHER PUBLICATIONS

English Translation of Search Report for Chinese Patent Application No. 201080060381.2, dated Jul. 3, 2013 (2 pages).
English Translation of Office Action for Chinese Patent Application No. 200980145368.4, mailed Nov. 27, 2013 (8 pages).
Extended European Search Report for European Application No. 10827667.6, dated Jul. 23, 2013 (8 pages).
International Preliminary Report on Patentability for International Application No. PCT/US2011/023930, issued Aug. 7, 2012 (1 page).
International Preliminary Report on Patentability and Written Opinion of the International Searching Authority for International Application No. PCT/US2010/055164, dated May 8, 2012 (8 pages).
International Search Report for International Application No. PCT/US2010/055164, mailed Jul. 29, 2011 (6 pages).
Office Action in Japanese Patent Application No. 2011-529275 mailed Dec. 17, 2013 (with English Translation) (6 pages).
Written Opinion of the International Searching Authority for International Application No. PCT/US2011/023930, mailed Sep. 29, 2011 (4 pages).

* cited by examiner

PACAP38:

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH2

(SEQ ID NO:1)

PACAP27:

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-NH2   (SEQ ID NO:2)

VIP:

His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH2   (SEQ ID NO:3)

FIG. 1

SEQUENCE LISTING

```
<160> NUMBER OF SEQ ID NOS: 27

<210> SEQ ID NO 1
<211> LENGTH: 38
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MOD_RES
<222> LOCATION: (38)..(38)
<223> OTHER INFORMATION: AMIDATION

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 27
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MOD_RES
<222> LOCATION: (27)..(27)
<223> OTHER INFORMATION: AMIDATION
```

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 3
<211> LENGTH: 28
<212> TYPE: PRT
<213> ORGANISM: Artificial
<220> FEATURE:
<223> OTHER INFORMATION: Description of Artificial Sequence VIP
<220> FEATURE:
<221> NAME/KEY: MOD_RES
<222> LOCATION: (28)..(28)
<223> OTHER INFORMATION: AMIDATION

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 27
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (27)..(27)
<223> OTHER INFORMATION: AMIDATION

<400> SEQUENCE: 4

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

<210> SEQ ID NO 5
<211> LENGTH: 27
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (27)..(27)
<223> OTHER INFORMATION: The last amino acid in this peptide has a
      functional group of OH

<400> SEQUENCE: 5

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

```
<210> SEQ ID NO 6
<211> LENGTH: 28
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (28)..(28)
<223> OTHER INFORMATION: AMIDATION

<400> SEQUENCE: 6

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly
            20                  25

<210> SEQ ID NO 7
<211> LENGTH: 28
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (28)..(28)
<223> OTHER INFORMATION: The last amino acid in this peptide has a
      functional group of OH

<400> SEQUENCE: 7

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly
            20                  25

<210> SEQ ID NO 8
<211> LENGTH: 29
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (29)..(29)
<223> OTHER INFORMATION: AMIDATION

<400> SEQUENCE: 8

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys
            20                  25

<210> SEQ ID NO 9
<211> LENGTH: 29
<212> TYPE: PRT
<213> ORGANISM: Artificial
<220> FEATURE:
<223> OTHER INFORMATION: Description of Artificial Sequence PACAP
```

```
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (29)..(29)
<223> OTHER INFORMATION: The last amino acid in this peptide has a
      functional group of OH

<400> SEQUENCE: 9

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys
            20                  25

<210> SEQ ID NO 10
<211> LENGTH: 30
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (30)..(30)
<223> OTHER INFORMATION: AMIDATION

<400> SEQUENCE: 10

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg
            20                  25                  30

<210> SEQ ID NO 11
<211> LENGTH: 30
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (30)..(30)
<223> OTHER INFORMATION: The last amino acid in this peptide has a
      functional group of OH

<400> SEQUENCE: 11

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg
            20                  25                  30

<210> SEQ ID NO 12
<211> LENGTH: 31
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
```

```
<221> NAME/KEY: MOD_RES
<222> LOCATION: (31)..(31)
<223> OTHER INFORMATION: AMIDATION

<400> SEQUENCE: 12

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr
            20                  25                  30

<210> SEQ ID NO 13
<211> LENGTH: 31
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (31)..(31)
<223> OTHER INFORMATION: The last amino acid in this peptide has a
      functional group of OH

<400> SEQUENCE: 13

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr
            20                  25                  30

<210> SEQ ID NO 14
<211> LENGTH: 32
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (32)..(32)
<223> OTHER INFORMATION: AMIDATION

<400> SEQUENCE: 14

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

<210> SEQ ID NO 15
<211> LENGTH: 32
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (32)..(32)
<223> OTHER INFORMATION: The last amino acid in this peptide has a
      functional group of OH

<400> SEQUENCE: 15
```

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

<210> SEQ ID NO 16
<211> LENGTH: 33
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (33)..(33)
<223> OTHER INFORMATION: AMIDATION

<400> SEQUENCE: 16

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln

<210> SEQ ID NO 17
<211> LENGTH: 33
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (33)..(33)
<223> OTHER INFORMATION: The last amino acid in this peptide has a
      functional group of OH

<400> SEQUENCE: 17

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln

<210> SEQ ID NO 18
<211> LENGTH: 34
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (34)..(34)
<223> OTHER INFORMATION: AMIDATION

<400> SEQUENCE: 18

His Ser Asp Gly Ile Phe Thr Asp Ser Tyr Ser Arg Tyr Arg Lys Gln

```
1               5                  10                 15
Xaa Ala Val Lys Lys Tyr Leu Ala Ala Val Leu Gly Lys Arg Tyr Lys
            20                 25                 30

Gln Arg

<210> SEQ ID NO 19
<211> LENGTH: 34
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (34)..(34)
<223> OTHER INFORMATION: The last amino acid in this peptide has a
      functional group of OH

<400> SEQUENCE: 19

His Ser Asp Gly Ile Phe Thr Asp Ser Tyr Ser Arg Tyr Arg Lys Gln
1               5                  10                 15

Xaa Ala Val Lys Lys Tyr Leu Ala Ala Val Leu Gly Lys Arg Tyr Lys
            20                 25                 30

Gln Arg

<210> SEQ ID NO 20
<211> LENGTH: 35
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (35)..(35)
<223> OTHER INFORMATION: AMIDATION

<400> SEQUENCE: 20

His Ser Asp Gly Ile Phe Thr Asp Ser Tyr Ser Arg Tyr Arg Lys Gln
1               5                  10                 15

Xaa Ala Val Lys Lys Tyr Leu Ala Ala Val Leu Gly Lys Arg Tyr Lys
            20                 25                 30

Gln Arg Val
        35

<210> SEQ ID NO 21
<211> LENGTH: 35
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (35)..(35)
<223> OTHER INFORMATION: The last amino acid in this peptide has a
      functional group of OH

<400> SEQUENCE: 21
```

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val
        35

<210> SEQ ID NO 22
<211> LENGTH: 36
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (36)..(36)
<223> OTHER INFORMATION: AMIDATION

<400> SEQUENCE: 22

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys
        35

<210> SEQ ID NO 23
<211> LENGTH: 36
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (36)..(36)
<223> OTHER INFORMATION: The last amino acid in this peptide has a
      functional group of OH

<400> SEQUENCE: 23

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys
        35

<210> SEQ ID NO 24
<211> LENGTH: 37
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (37)..(37)

<223> OTHER INFORMATION: AMIDATION

<400> SEQUENCE: 24

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn
        35

<210> SEQ ID NO 25
<211> LENGTH: 37
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MISC_FEATURE
<222> LOCATION: (37)..(37)
<223> OTHER INFORMATION: The last amino acid in this peptide has a
      functional group of OH

<400> SEQUENCE: 25

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn
        35

<210> SEQ ID NO 26
<211> LENGTH: 38
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu
<220> FEATURE:
<221> NAME/KEY: MOD_RES
<222> LOCATION: (38)..(38)
<223> OTHER INFORMATION: AMIDATION

<400> SEQUENCE: 26

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn Lys
        35

<210> SEQ ID NO 27
<211> LENGTH: 38
<212> TYPE: PRT
<213> ORGANISM: Artificial
<220> FEATURE:
<223> OTHER INFORMATION: Description of Artificial Sequence PACAP
<220> FEATURE:
<221> NAME/KEY: MISC_FEATURE
<222> LOCATION: (17)..(17)
<223> OTHER INFORMATION: Xaa = Met, Gly, Ser, Phe, Nle, Arg, or Glu

```
<220> FEATURE:
<221> NAME/KEY: MISC_FEATURE
<222> LOCATION: (38)..(38)
<223> OTHER INFORMATION: The last amino acid in this peptide has a
      functional group of OH

<400> SEQUENCE: 27

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn Lys
            35
```

TREATMENT OF RENAL DYSFUNCTION AND MULTIPLE MYELOMA USING PACAP COMPOUNDS

CROSS REFERENCE TO RELATED APPLICATIONS

The present application claims priority to U.S. Provisional Application Ser. No. 60/589,674, filed Jul. 21, 2004, which is incorporated by reference herein in its entirety.

1. FIELD OF THE INVENTION

The present invention relates to methods and compositions for the treatment, management, or prevention of renal dysfunction and/or multiple myeloma in mammals. The methods of the invention comprise the administration of an effective amount of one or more pituitary adenylate cyclase activating polypeptide ("PACAP") compounds, which includes PACAP, vasoactive intestinal peptide ("VIP"), their agonists, analogs, fragments, or derivatives, having one or more PACAP activities. The invention also provides pharmaceutical compositions comprising one or more PACAP compounds of the invention either alone or in combination with one or more other prophylactic/therapeutic agents useful in therapy for the treatment, management, or prevention of renal dysfunction and/or multiple myeloma.

2. BACKGROUND OF THE INVENTION

The fundamental renal (kidney) filtration unit, which removes harmful waste products from the blood and produces urine, is a complex anatomical structure called a nephron. Human kidneys serve to convert in excess of 1700 liters of blood per day into about 1 liter of urine; each human kidney contains approximately one million nephrons. Each nephron is comprised of a vascular component and a tubular component. The glomerulus, the principal vascular component, is a convoluted semipermeable capillary network through which part of the water and solutes are filtered from the blood passing through. The glomerular basement membrane acts like a sieve to retain cells and large protein molecules, while passing water and soluble wastes. The filtered fluid (also called nephritic filtrate), which is almost identical in composition to plasma, then enters the tubular portion of the nephron. The tubular portion is comprised of a sequential series of ducts, including a proximal tubule, a loop of Henle, a distal tubule, and a collecting tubule, which lead to a ureter and thence to the urinary bladder. Much of the water, salts, and nutrients initially passed by the glomerulus are reclaimed by the nephron via various transport processes before the filtrate completes its transit to the bladder.

Renal dysfunction, or when associated with a disease, renal disease (disease of the kidneys) can have many causes, including but not limited to: drugs, toxic substances, antibiotics, infections, diabetes, and cancer. The kidney is a highly complex structure of primarily four systems (including vascular, glomerular, tubular, and interstitial regions), and the anatomical interdependence of these structures implies that damage to one structure usually affects the others secondarily. Thus, there is a tendency for all forms of chronic renal damage to eventually destroy all four systems. In addition, because the kidneys have a large functional reserve, much damage may occur before clinical symptoms are manifest. Thus, kidney disease is commonly insidious, and detection of early signs and symptoms is especially important.

Multiple myeloma, a malignant tumor of plasma cells, is commonly associated with osteolytic lesions (lytic bone loss), recurrent bacterial infections, anemia, and chronic interstitial nephritis (inflammation of the interstitial tissue of the kidney) leading to renal failure. The etiology of multiple myeloma (also called myeloma) is unknown, but the frequency of this disease in patients with monoclonal gammopathy of undetermined significance (marked by the presence in serum of monoclonal immunoglobulins IgA or IgG) is high. Moreover, the presence in families of both multiple myeloma and monoclonal gammopathy of undetermined significance suggests a genetic link between these diseases.

The American Cancer Society estimates that more than 15,000 new cases of multiple myeloma will be diagnosed in 2004, and that more than 11,000 Americans will die of multiple myeloma in 2004. American Cancer Society, *Cancer Facts & Figures* 2004.

In multiple myeloma, the source of renal involvement is overproduction of antibody light chains (Bence-Jones proteins), which aggregate in the distal convoluted tubules and collecting ducts of the kidneys, forming proteinaceous casts. Antibodies are produced by immune cells called plasma cells, which arise from activated B lymphocytes (B cells). Each B cell produces a unique receptor (B cell receptor), specific for a foreign substance and arrayed on the cell surface. When a B cell receptor recognizes its cognate antigen (foreign substance), the cell carrying that receptor becomes activated, re-enters the cell cycle, and produces many clonal copies of itself. These clones mature into plasma cells, which reside principally in the bone marrow. Plasma cells are specialized to produce copies of the B cell receptor, which are then released to the bloodstream as antibodies (immunoglobulins). Immunoglobulins are comprised of four protein chains: two long chains called heavy chains, and two shorter chains called light chains.

In multiple myeloma, the mother B cell suffers genetic damage resulting in suppression of or insensitivity to the normal restraints on cell division. Thus, the daughter plasma cells produced by such a B cell are malignant—they continue to divide unchecked, creating more malignant plasma cells, and generating multiple copies of the same immunoglobulin (also called monoclonal protein, M protein, or paraprotein) in excess amounts. An elevated level of M protein in the blood is a hallmark of multiple myeloma, but up to 20% of patients with myeloma produce only the light chain portion of the immunoglobulins, called Bence-Jones proteins (a subset of the "M protein" group). In such patients, these free monoclonal light chains are found principally in the urine instead of the blood, having passed through the renal filtration mechanisms. Bence-Jones proteins may precipitate from solution while passing through the distal convoluted tubules and collecting ducts of the kidney, forming proteinaceous deposits (also called "casts") therein. These casts clog the renal tubular network, cause damage to surrounding epithelium, and initiate inflammatory cascades, leading eventually to renal failure. Hypercalcemia, hypercalciuria, and hyperuricemia may also contribute further damage. "Myeloma kidney" is characterized histologically by interstitial fibrosis and hyaline casts surrounded by epithelial cells or multinucleate giant cells.

Pituitary adenylate cyclase activating polypeptide (PACAP) was originally isolated from ovine (sheep) hypothalamic tissues based on its ability to activate adenylate cyclase in rat pituitary cell cultures. Miyata et al. *Biochem Biophys Res Commun.* 164: 567 (1989). PACAP is a neurotransmitter and neuroendocrine hormone, and exists in two active forms: a long form, with 38 amino acids (PACAP38), and a C-terminally truncated form with 27 amino acids (PACAP27). Miyata et al. *Biochem Biophys Res Commun.* 170: 643 (1990). The amino acid sequences for these two versions are shown in FIG. 1 (SEQ ID NO:1 and SEQ ID NO:2). PACAP is a member of the secretin/glucagon/vasoactive intestinal peptide family, the N-terminal region being 68% homologous to VIP (SEQ ID NO:3), yet its adenylate cyclase stimulating activity in cultured pituitary cells, neurons and astrocytes is about 1,000-10,000 times greater than VIP. Miyata et al. (1990), supra. PACAP is a pleiotropic neuropeptide, exhibiting a number of neurotrophic activities in different organs and tissues. For example, PACAP enhances proliferation and differentiation of sympathetic neuroblasts, stimulates neurite outgrowth of an adrenal chromaffin cell line (PC-12 pheochromocytoma cells), and stimulates growth of astrocytes. Arimura A. *Regul Pept.* 37: 285 (1992); Okazaki K, et al. *FEBS Lett.* 298: 49 (1992). The in vivo cytoprotective action of PACAP has been investigated in rats with transient forebrain ischemia. Uchida et al., *Soc Neurosci Abst.*, Vol. 20, 1994 (Abstract No. 193.10).

One of the activities of PACAP is its ability to bind one or more PACAP receptors. There are at least three known PACAP receptors: $PAC_1$-R (type I PACAP receptor); $VPAC_1$-R (type II PACAP receptor, or type I VIP receptor); and $VPAC_2$-R (type II VIP receptor, or VIP2). Gottschall P E, et al. *Endocrinology.* 127: 272 (1990); Shivers B D, et al. *Endocrinology.* 128: 3055 (1991); Arimura A. *Trends Endocrinol Metab.* 3: 288 (1992). PAC1-R, which is found in the hypothalamus, brain stem, pituitary, adrenal gland, pancreas, and testes, specifically binds to PACAP with high affinity, but does not bind to VIP. Ogi K, et al. *Biochem Biophys Res Commun.* 196: 1511 (1993). $VPAC_1$-R and $VPAC_2$-R both bind PACAP and VIP with similar high affinities. Sreedharan S P, et al. *Proc Natl Acad Sci USA.* 92: 2939 (1995); Svoboda M, et al. *Biochem Biophys Res Commun.* 205: 1617 (1994).

Standard treatments for multiple myeloma include: chemotherapy; autologous stem cell transplantation; and thalidomide. Dexamethasone (a steroid) is currently used to protect against renal damage induced by the light chains, and to suppress tumor cell proliferation. However, the side effects of long-term dexamethasone administration are of serious concern. In particular, chronic dexamethasone treatment can cause osteoporosis, thus reducing its utility in myeloma therapy because a major sequela of myeloma is bone resorption. Thus there is a need to obtain an improvement over existing therapies for multiple myeloma and renal disease.

Citation or discussion of a reference herein shall not be construed as an admission that such is prior art to the present invention.

3. SUMMARY OF THE INVENTION

The inventors have found that PACAP compounds are extremely effective in protecting and/or rescuing renal cells and for the treatment or prevention of renal dysfunction and multiple myeloma. Without being bound by a particular mechanism, the therapeutic effects may be mediated by inhibition of MAP kinase and/or NFκB activation. Pituitary adenylate cyclase activating polypeptides—particularly PACAP38—are pleiotropic. PACAP38 either suppresses or activates MAPK, depending on which receptor the PACAP interacts. PACAP38 may also interact with immune cells directly, modulating their production of cytokines (including TNF-α and IL6).

Accordingly, the present invention relates to methods and compositions for the treatment, management, and prevention of renal cell damage that relates to renal dysfunction and/or caused by multiple myeloma. The method comprises administering an effective amount of one or more PACAP compounds which includes PACAP, VIP, their agonists, analogs, fragments, or derivatives, having one or more PACAP activities, for the inhibition of a pathology-causing cell phenotype (e.g., a pathology-causing epithelial cell phenotype) in renal cells, particularly renal tubule cells, and multiple myeloma. For histopathologic comparison of renal cells of various renal diseases, see Kucher et al. *J. Cutan Path.* 32(7):484-90 (2005).

PACAP compounds are extremely effective in protecting and/or rescuing renal cells in a concentration-dependent manner. Thus, the present invention relates to a method of treatment of renal cells at a concentration of about $10^{-13}$ M to $10^4$ M of the PACAP compound. When the renal cells are in culture, the concentration of the PACAP compound is preferably between about $10^{-13}$M to $10^{-7}$ M in the culture medium. When the renal cells are in the tissues of a subject, the concentration of the PACAP compound is preferably between about $10^{-13}$ M to $10^{-7}$ in the interstitial space or blood. The inventors have discovered that within the generally effective concentration range of the composition of this invention, there is a peak effectiveness, below which the effectiveness of the composition falls off to a significant degree. In preferred embodiment, the concentration of the PACAP composition of the present invention is between about $10^{-13}$M and about $10^{-7}$ M, which permits treatment of the subject with minimal risk of adverse side effects from the treatment. In a preferred embodiment, the concentration of the PACAP compound is about $10^{-9}$M. The present discovery makes possible the use of the composition of the invention in low concentrations to provide substantial protection and rescue of renal cells. In specific embodiments, the composition of the invention protects renal tubule epithelial cells from injury or death. The injury or death of the renal cells may be due to overload of proteins, including monoclonal protein, paraprotein, M protein, and Bence-Jones proteins or those entering the renal tubular system due to impaired glomerular filtration, various toxic agents such as mercury and antibiotics, enhanced immune reaction including rejection of implanted kidney, and other causes.

Similar to its effectiveness in protecting and/or rescuing renal cells, PACAP is also very effective for the treatment, management, or prevention of the proliferation of multiple myeloma cells in a concentration-dependent manner. Thus, the present invention also involves a method of treatment, management, or prevention of the proliferation of multiple myeloma cells in which the concentration of the PACAP compound is between about $10^{-13}$M and $10^{-7}$ M. In one embodiment, when the cells that are to be treated are in culture, the effective amount is about $10^{-13}$ M to about $10^{-7}$ M in the culture medium. In another embodiment, when the myeloma cells are in the tissue of a subject, the concentration of the PACAP compound is measured in the interstitial space or blood. The preferred concentration of PACAP compounds for treatment is about $10^{-13}$ to about $10^{-7}$ M. At this concentration range, the subject has minimal risk of side effects from the treatment. The present discovery makes possible the use of the composition of the present invention in low concentrations to provide very substantial inhibition of multiple myeloma cell growth.

The composition of the present invention includes a composition comprising one or more PACAP compounds, which includes PACAP, in either of its forms (PACAP38 and PACAP27), VIP, as well as any of their peptide or non-peptide agonists, analogs, fragments, or derivatives, having one or more PACAP activities, which include but are not limited to, binding to at least one PACAP receptor ($PAC_1$-R, $VPAC_1$-R, and $VPAC_2$-R). In a preferred embodiment, PACAP, VIP, and agonists, analogs, fragments or derivatives thereof bind to $VPAC_2$-R (type II VIP receptor). Preferably, the PACAP agonist, analog, fragment or derivative thereof is a polypeptide, or a salt or derivative thereof, which contains at least twelve consecutive amino acids corresponding to a portion of the amino acid sequence of PACAP38 in FIG. 1, and which binds to at least one PACAP receptor. As used herein a "$PACAP_{12}$ agonist" refers to a polypeptide, or salt or derivative thereof, which has at least 12 consecutive amino acids corresponding to a portion of the amino acid sequence of PACAP38, as shown in FIG. 1, and which binds to at least one PACAP receptor. Similarly, the terms "$PACAP_{23}$ agonist" and "$PACAP_{27}$ agonist" refer to polypeptides, or salts or derivatives thereof, which have at least 23 and 27 consecutive amino acids, respectively, corresponding to a portion of the amino acid sequence of PACAP38, as shown in FIG. 1, and which bind to at least one PACAP receptor. Determination of the amino acid sequence of the polypeptide, and determination of whether the polypeptide binds to a PACAP receptor, are both well within the skill in the art.

The composition of the present invention may be administered intravenously or otherwise into the blood, to deliver the PACAP compounds in concentration effective to treat, protect and/or rescue renal cells. In another embodiment, the composition of the invention may be administered at an effective concentration so that the PACAP may be in contact with the myeloma cells so as to suppress and/or inhibit the cancerous plasma cells.

The present invention provides a method of treating, managing, or preventing renal dysfunction, the method comprises administering to a subject an effective amount of one or more PACAP compounds, wherein the PACAP compounds bind to one or more PACAP receptors or decrease a pathology-causing cell phenotype. In specific embodiments, the renal dysfunction is caused by ischemia, reperfusion, trauma, hemorrhage, infection, administration of antibiotic, or exposure to a toxic substance. In specific embodiments, the renal dysfunction is associated with a disease. In a specific embodiment, the disease is multiple myeloma. In another embodiment, the disease is diabetes. In other specific embodiments, the renal dysfunction is chronic renal failure, acute renal failure, or myeloma kidney. In certain embodiments, the pathology-causing cell phenotype is an increase in cell viability. In other embodiments, the pathology-causing cell phenotype is an inhibition of hyperproliferation of cells. In preferred embodiments, the pathology-causing cell phenotype is a decrease in production of TNF-α and/or IL-6. In other embodiments, the pathology-causing cell phenotype is an activation of NFκB.

The present invention is directed to a method of treating, managing, or preventing a hyperproliferative disease, the method comprises administering to a subject an effective amount of one or more PACAP compounds, wherein the PACAP compounds bind to one or more PACAP receptors or decrease a pathology-causing cell phenotype. In a preferred embodiment, the hyperproliferative disease is multiple myeloma.

The present invention is also directed to a method of protecting or rescuing renal tubule cells from damage, the method comprises administering to a subject an effective amount of one or more PACAP compounds, wherein the PACAP compounds bind to one or more PACAP receptors or decrease a pathology-causing cell phenotype. In specific embodiments, the damage is caused by ischemia, reperfusion, trauma, hemorrhage, exposure to toxic agents or excess proteins. In other specific embodiments, the protein is monoclonal protein, paraprotein, M protein or Bence-Jones protein.

The present invention is directed to a method of treating, managing, or preventing the progression of myeloma, the method comprises administering to a subject an effective amount of one or more PACAP compounds, wherein the PACAP compounds bind to one or more PACAP receptors or decrease a pathology-causing cell phenotype.

The present invention is directed to a method of treating, managing, or preventing a renal disease caused by the activation of NFκB, the method comprises administering to a subject an effective amount of one or more PACAP compounds, wherein the PACAP compounds bind to one or more PACAP receptors or decrease a pathology-causing cell phenotype.

The present invention is directed to a method of treating, managing, or preventing a disorder associated with kidney damage, the method comprises administering to a subject an effective amount of one or more PACAP compounds, wherein the PACAP compounds bind to one or more PACAP receptors or decrease a pathology-causing cell phenotype. In specific embodiments, the disorder is hypertension, sickle cell anemia, Sjogren's syndrome, lupus, polycystic kidney disease, chronic renal failure, acute renal failure, diabetes, myeloma, hemolytic uremic syndrome, lupus nephritis or Henoch-Schonlein purpura nephritis.

4. BRIEF DESCRIPTION OF DRAWINGS

FIG. 1 shows the primary structure PACAP38 (SEQ ID NO:1), PACAP27 (SEQ ID NO:2), and VIP (SEQ ID NO:3).

FIGS. 2A-D demonstrate the beneficial effect of PACAP38 on human renal tubule cell morphology and survival in vitro, in the presence or absence of light chains. A—Control human renal tubule cell morphology in the absence of light chains. B—Addition of light chains (50 μM) to cultures for 3 days produced marked cell damage. C—Human renal tubule cell morphology was dramatically attenuated by the addition of PACAP38 (10 nM). D—Incubation with PACAP38 alone did not alter the human renal tubule cell morphology.

Figure 3:
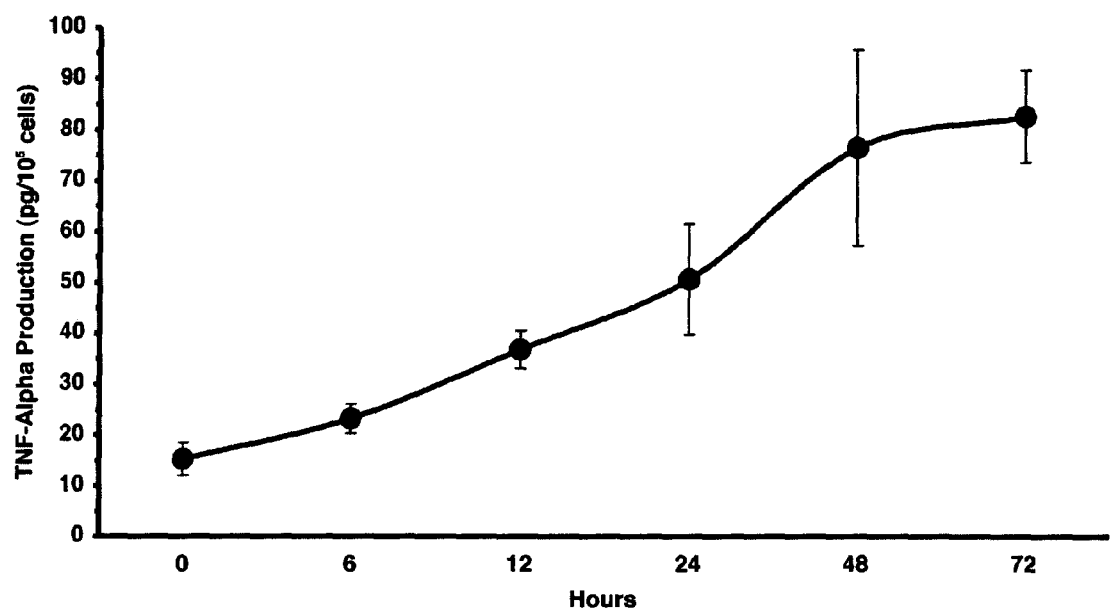

FIG. 3 illustrates the time-course of tumor necrosis factor alpha (TNF-α) production by human proximal tubule cells in vitro, when co-incubated with immunoglobulin light chains (50 μM). TNF-α production increased gradually, reaching maximum levels after 48 hours. The data are mean±SEM.

Figure 4:
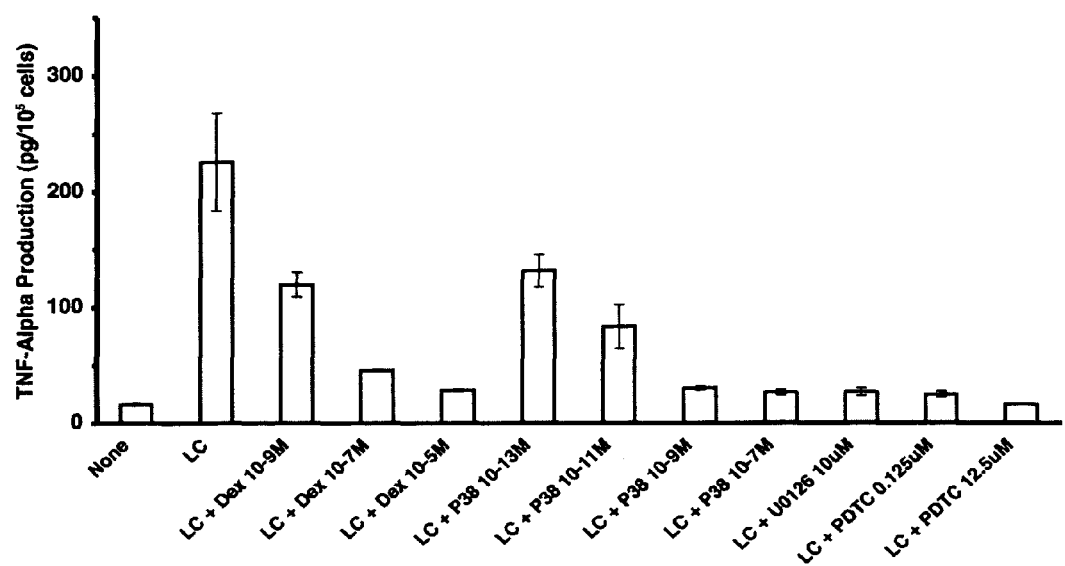

FIG. 4 demonstrates the effects of either dexamethasone (Dex), PACAP38, U0126 (MEK1/2 inhibitor), or PDTC (NFκB inhibitor) on TNF-α production by human proximal tubule cells in vitro, when co-incubated for 72 hours with immunoglobulin light chain. Suppression of TNF-α production by dexamethasone or PACAP38 (P38) was dose dependent and reached a maximum at $10^{-7}$ M PACAP38. The suppressive potency of PACAP38 in this assay is 10,000 times greater than that of an equivalent concentration of dexamethasone. The data are mean±SEM.

Figure 5:
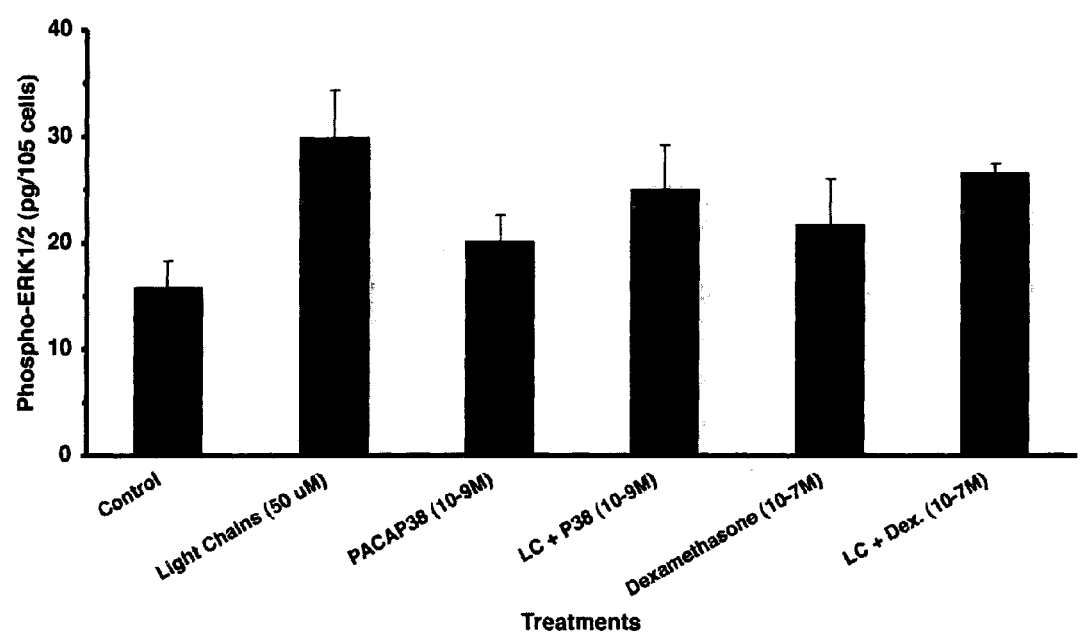

FIG. 5 shows the effects of either dexamethasone or PACAP38 on light chain-induced activation of ERK1/2 (as reflected by phospho-ERK1/2 ELISA) in human proximal tubule cells. The dexamethasone and PACAP38 concentrations used ($10^{-7}$ M and $10^{-9}$ M, respectively) showed comparable activity in their ability to suppress light chain-induced TNF-α production (See FIG. 4). However, neither dexamethasone nor PACAP38 suppressed light chain-induced ERK1/2 activation significantly. The data are mean±SEM.

Figure 6:
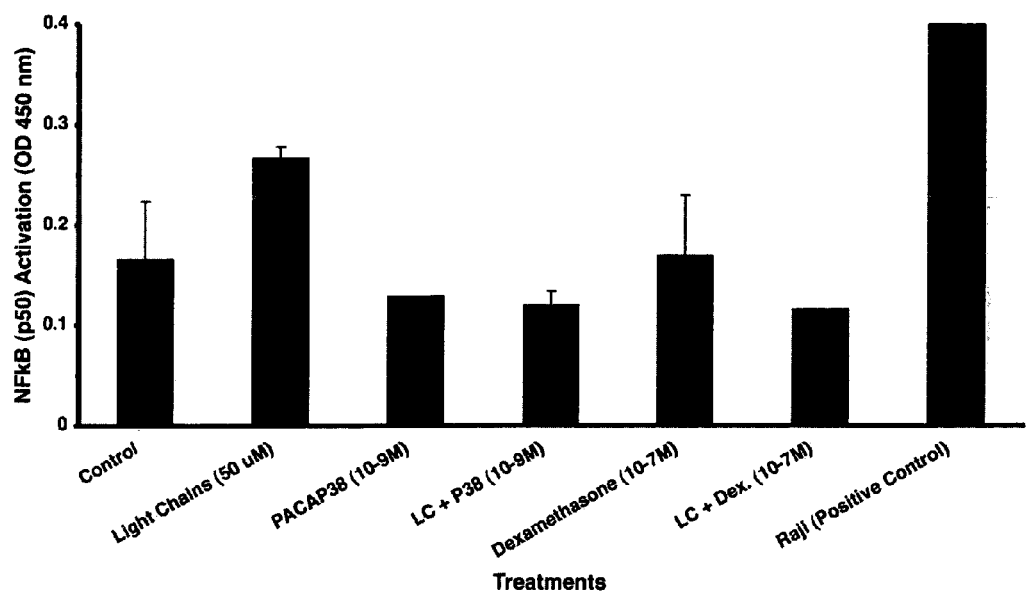

FIG. 6 shows the effects of either dexamethasone or PACAP38 on light-chain-induced activation of the p50 subunit of NFκB in human proximal tubule cells. The dexamethasone and PACAP38 concentrations used ($10^{-7}$ M and $10^{-9}$ M, respectively) showed comparable activity in their ability to suppress light chain-induced TNF-α production (See FIG. 4). Light chains induced activation of NFκB p50 subunit, which was suppressed by both dexamethasone and PACAP38. The data are mean±SEM.

Figure 7:
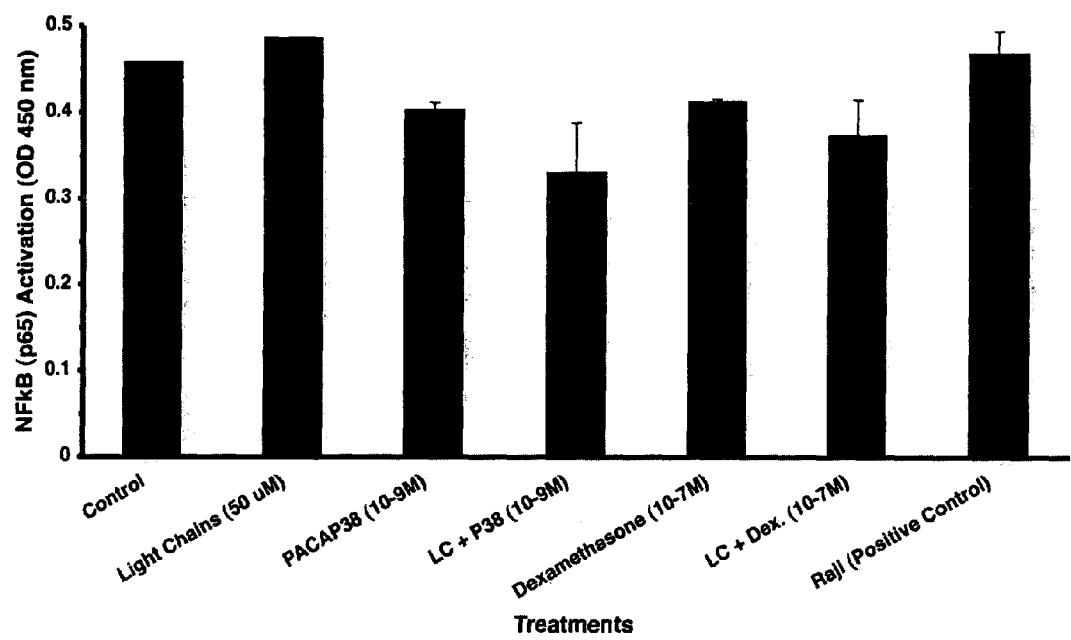

FIG. 7 shows the effects of either dexamethasone or PACAP38 on light-chain-induced activation of the p65 subunit of NFκB in human proximal tubule cells. The dexamethasone and PACAP38 concentrations used ($10^{-7}$ M and $10^{-9}$ M, respectively) showed comparable activity in their ability to suppress light chain-induced TNF-α production (See FIG. 4). Light chains did not induce significant activation of NFκB p65 subunit, yet both dexamethasone and PACAP38 suppressed NFκB p65 subunit activity slightly. The data are mean±SEM.

Figure 8:
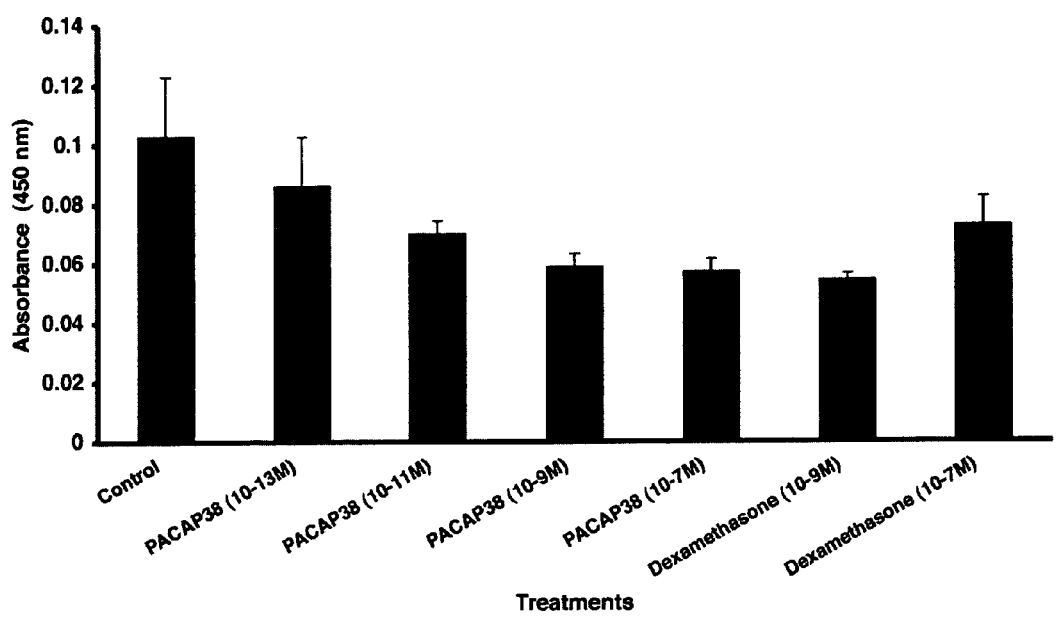

FIG. 8 demonstrates the effects of either dexamethasone or PACAP38 on NCI-H929 human myeloma cell line growth, as measured by incorporation of 5-bromo-2-deoxyuridine (BrdU). PACAP38 demonstrates dose-dependent suppression of myeloma cell growth at concentrations significantly lower than dexamethasone. The data are mean±SEM.

Figure 9:
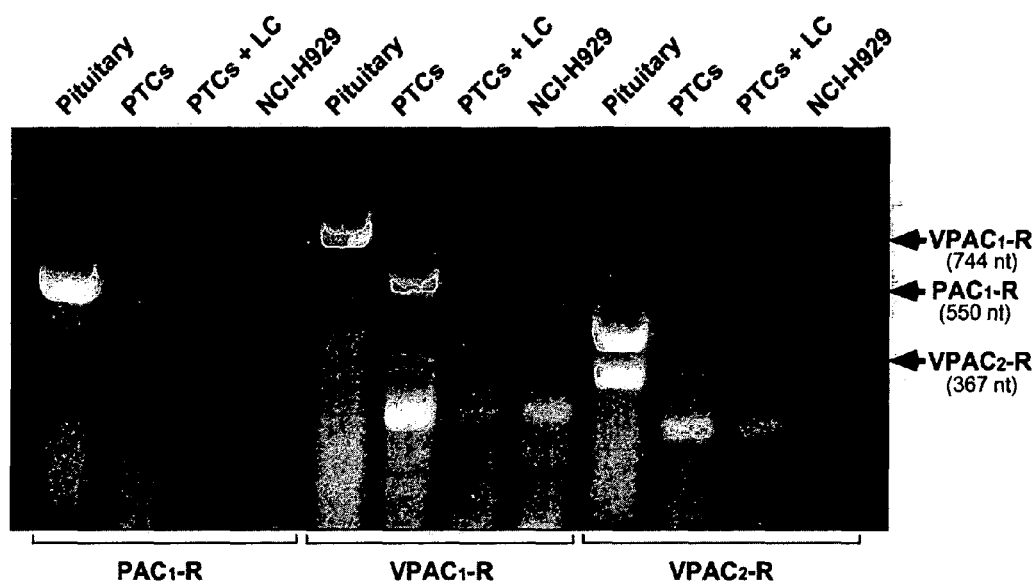

FIG. 9 shows the results of RT-PCR analysis for the presence of $PAC_1$, $VPAC_1$, and $VPAC_2$ receptors in pituitary, renal proximal tubule cells (PTCs), PTCs incubated with light chains, and human multiple myeloma cells (NCI-H929). The pituitary expresses all three receptor types, and was used as a positive control. Neither $PAC_1$-R nor $VPAC_1$-R was expressed by PTCs or myeloma cells. However, a faint band corresponding to $VPAC_2$-R was observed for both PTCs and myeloma cells.

Figure 10:
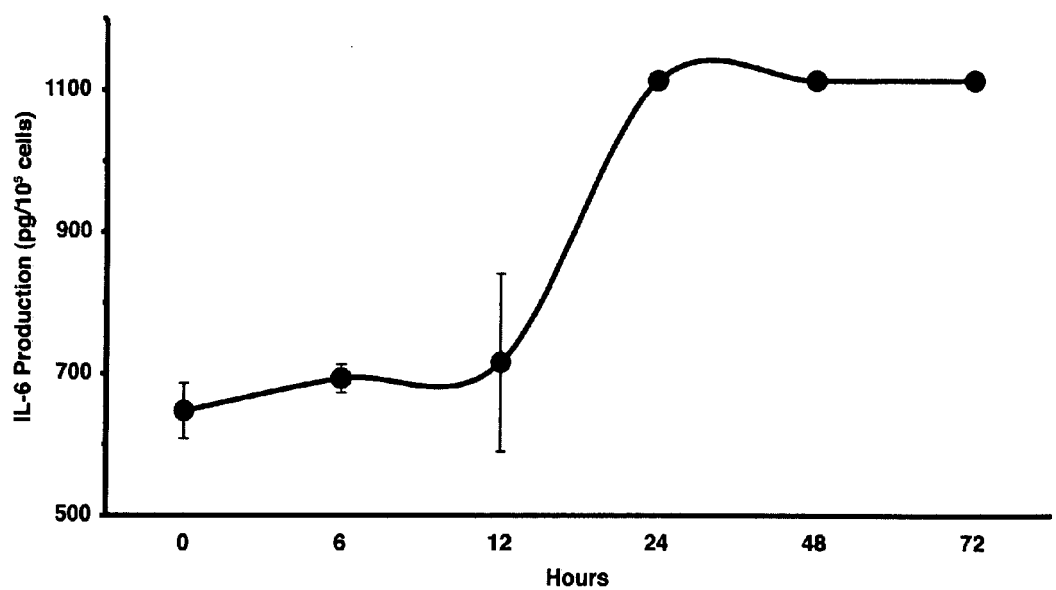

FIG. 10 illustrates the time-course of interleukin 6 (IL-6) production by human proximal tubule cells in vitro, when co-incubated with immunoglobulin light chains (50 μM). IL-6 production increased significantly after 12 hours, reaching a plateau after 24 hours. The data are mean±SEM.

Figure 11:
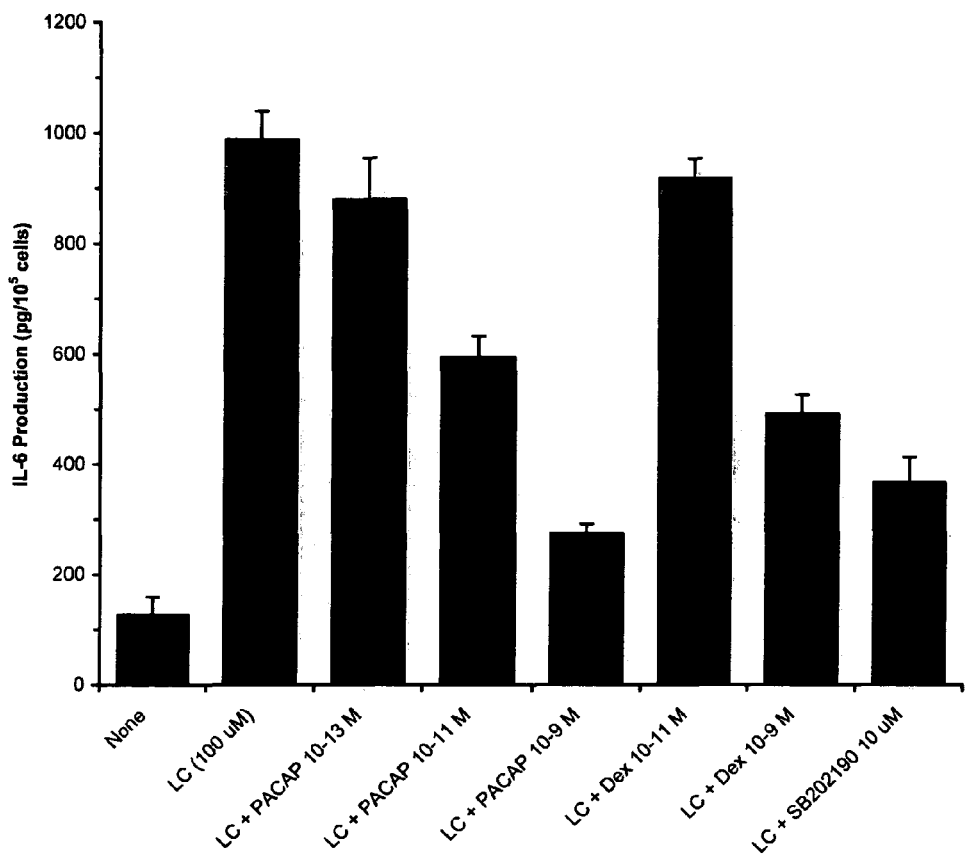

FIG. 11 demonstrates the effects of PACAP38, dexamethasone, and SB202190 (specific inhibitor of p38 MAPK, a stress-activated protein kinase) on light chain-induced IL-6 production by human proximal tubule cells in vitro. Suppression of IL-6 production by dexamethasone and PACAP38 was dose dependent. PACAP38 is significantly more effective at suppressing IL-6 production than dexamethasone. The data are mean±SEM.

Figure 12:
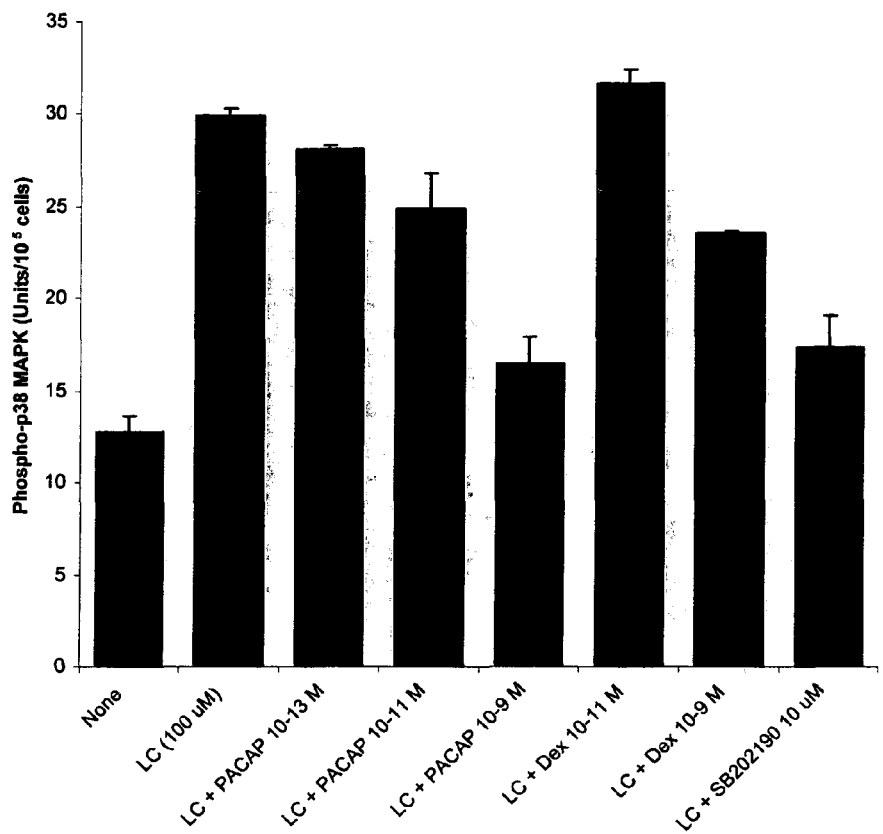

FIG. 12 demonstrates the effects of PACAP38, dexamethasone, or SB202190 (p38 MAPK inhibitor) on light chain-induced activation of p38 MAPK in human proximal tubule cells in vitro (as measured by ELISA). Incubation with light chains caused significant activation of p38 MAPK. Both PACAP38 and dexamethasone suppressed p38 MAPK activation in a dose-dependent manner, although PACAP38 was significantly more effective at comparable doses. The suppressive potency of PACAP38 in this assay was comparable to that of the specific p38 MAPK inhibitor itself. The data are mean±SEM.

4.1 Sequences

Below is a brief summary of the sequences presented in the accompanying sequence listing, which is incorporated by reference herein in its entirety:

SEQ ID NO:1 is an amino acid sequence of a PACAP that can be used according to the present invention.
SEQ ID NO:2 is an amino acid sequence of a PACAP that can be used according to the present invention.
SEQ ID NO:3 is an amino acid sequence of a VIP that can be used according to the present invention.
SEQ ID NO:4 is an amino acid sequence of a PACAP that can be used according to the present invention.
SEQ ID NO:5 is an amino acid sequence of a PACAP that can be used according to the present invention.
SEQ ID NO:6 is an amino acid sequence of a PACAP that can be used according to the present invention.
SEQ ID NO:7 is an amino acid sequence of a PACAP that can be used according to the present invention.
SEQ ID NO:8 is an amino acid sequence of a PACAP that can be used according to the present invention.
SEQ ID NO:9 is an amino acid sequence of a PACAP that can be used according to the present invention.
SEQ ID NO:10 is an amino acid sequence of a PACAP that can be used according to the present invention.
SEQ ID NO:11 is an amino acid sequence of a PACAP that can be used according to the present invention.
SEQ ID NO:12 is an amino acid sequence of a PACAP that can be used according to the present invention.
SEQ ID NO:13 is an amino acid sequence of a PACAP that can be used according to the present invention.
SEQ ID NO:14 is an amino acid sequence of a PACAP that can be used according to the present invention.
SEQ ID NO:15 is an amino acid sequence of a PACAP that can be used according to the present invention.
SEQ ID NO:16 is an amino acid sequence of a PACAP that can be used according to the present invention.
SEQ ID NO:17 is an amino acid sequence of a PACAP that can be used according to the present invention.
SEQ ID NO:18 is an amino acid sequence of a PACAP that can be used according to the present invention.
SEQ ID NO:19 is an amino acid sequence of a PACAP that can be used according to the present invention.
SEQ ID NO:20 is an amino acid sequence of a PACAP that can be used according to the present invention.
SEQ ID NO:21 is an amino acid sequence of a PACAP that can be used according to the present invention.
SEQ ID NO:22 is an amino acid sequence of a PACAP that can be used according to the present invention.
SEQ ID NO:23 is an amino acid sequence of a PACAP that can be used according to the present invention.
SEQ ID NO:24 is an amino acid sequence of a PACAP that can be used according to the present invention.
SEQ ID NO:25 is an amino acid sequence of a PACAP that can be used according to the present invention.
SEQ ID NO:26 is an amino acid sequence of a PACAP that can be used according to the present invention.
SEQ ID NO:27 is an amino acid sequence of a PACAP that can be used according to the present invention.

4.2 Definitions

As used herein, the term "agonist" refers to any molecule, including a protein, post-translationally modified protein, polypeptide, peptide, fragment, large molecule, or small molecule (less than 1000 daltons), that binds to one or more PACAP receptors.

As used herein, the term "analog" in the context of a polypeptide refers to a polypeptide that possesses a similar or identical function as a second polypeptide but does not necessarily comprise a similar or identical amino acid sequence or structure of the second polypeptide. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second polypeptide; (b) a polypeptide encoded by a nucleotide sequence that hybridizes under stringent conditions to a nucleotide sequence encoding a second polypeptide of at least twelve amino acid residues, at least 15 amino acid residues, at least 20 amino acid residues, at least 25 amino acid residues, at least 30 amino residues, at least 35 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second polypeptide. A polypeptide with similar structure to a second polypeptide refers to a polypeptide that has a similar secondary, tertiary or quaternary structure of the second polypeptide. The structure of a polypeptide can be determined by methods known to those skilled in the art, including but not limited to, X-ray crystallography, nuclear magnetic resonance, and crystallographic electron microscopy. Preferably, the polypeptide has one or more PACAP activities.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions x 100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, *Proc. Natl. Acad. Sci. U.S.A.* 87: 2264-2268, modified as in Karlin and Altschul, 1993, *Proc. Natl. Acad. Sci. U.S.A.* 90: 5873-5877. Such an algorithm is incorporated into the NBLAST and XBLAST programs of Altschul et al., 1990, *J. Mol. Biol.* 215: 403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, *Nucleic Acids Res.* 25: 3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, *CABIOS* 4: 11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "derivative" in the context of a polypeptides, refers to a polypeptide that comprises the amino acid sequence which has been altered by the introduction of amino acid residue substitutions, deletions, and/or additions.

The term "derivative" as used herein also refers to a polypeptide which has been modified, i.e., by the covalent attachment of a type of molecule to the polypeptide. For example, but not by way of limitation, a derivative of a polypeptide may be produced, e.g., by glycosylation, acetylation, pegylation, phosphorylation, amidation, derivatization by known protecting/blocking groups, proteolytic cleavage, linkage to a cellular ligand or other protein, etc. A derivative of a polypeptide may also be produced by chemical modifications using techniques known to those of skill in the art, including, but not limited to specific chemical cleavage, acetylation, formylation, etc. Further, a derivative of a polypeptide may contain one or more non-classical amino acids. A derivative of a polypeptide possesses an identical function(s) as the polypeptide from which it was derived.

As used herein, the term "derivative" in the context of PACAP polypeptide or VIP polypeptide refers to a polypeptide that comprises an amino acid sequence of a polypeptide or a fragment of a PACAP polypeptide or VIP polypeptide, respectively, that has been altered by the introduction of amino acid residue substitutions, deletions or additions (i.e., mutations). The term "derivative" as used herein in the context of PACAP polypeptide or VIP polypeptide also refers to a PACAP polypeptide or VIP polypeptide, or a fragment of a PACAP polypeptide or a VIP polypeptide, which has been modified, i.e, by the covalent attachment of any type of molecule to the polypeptide. For example, but not by way of limitation, a PACAP polypeptide or VIP polypeptide, or a fragment of a PACAP polypeptide or VIP polypeptide, may be modified, e.g., by glycosylation, acetylation, pegylation, phosphorylation, amidation, derivatization by known protecting/blocking groups, proteolytic cleavage, linkage to a cellular ligand or other protein, etc. A derivative of a PACAP polypeptide or VIP polypeptide, or a fragment of a PACAP polypeptide or VIP polypeptide, may be modified by chemical modifications using techniques known to those of skill in the art, including, but not limited to, specific chemical cleavage, acetylation, formylation, metabolic synthesis of tunicamycin, etc. Further, a derivative of a PACAP polypeptide or VIP polypeptide, or a fragment of a PACAP polypeptide or VIP polypeptide may contain one or more non-classical amino acids. In one embodiment, a polypeptide derivative possesses a similar or identical function as a PACAP or VIP polypeptide or a fragment of a PACAP or VIP polypeptide described herein. In another embodiment, a derivative of PACAP or VIP polypeptide or a fragment of a PACAP or VIP polypeptide has an altered activity when compared to an unaltered polypeptide.

As used herein, the term "fragments" in the context of PACAP or VIP polypeptides include a PACAP or VIP peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues of the amino acid sequence of a PACAP or VIP polypeptide.

As used herein, the term "fusion protein" refers to a polypeptide or protein that comprises the amino acid sequence of a first polypeptide or protein or fragment, analog or derivative thereof, and the amino acid sequence of a heterologous polypeptide or protein. In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent. For example, two different proteins, polypeptides, or peptides with immunomodulatory activity may be fused together to form a fusion protein. In a preferred embodiment, fusion proteins retain or have improved activity relative to the activity of the original polypeptide or protein prior to being fused to a heterologous protein, polypeptide, or peptide.

As used herein, the terms "hyperproliferative cell disorder," "hyperproliferative cell disease," "hyperproliferative disorder," and "hyperproliferative disease" and analogous terms refer to a disorder in which cellular hyperproliferation or any form of excessive cell accumulation causes or contributes to the pathological state or symptoms of the disorder. In an embodiment, the hyperproliferative cell disorder is characterized by hyperproliferating epithelial cells. In another embodiment, the hyperproliferative cell disorder is characterized by hyperproliferating renal tubule cell. In certain embodiments, the hyperproliferative cell disorder is not neoplastic. In certain embodiments, the hyperproliferative cell disorder is neoplastic. In a preferred embodiment, the hyperproliferative disorder is myeloma.

As used herein, the term "in combination" refers to the use of more than one therapies (e.g., prophylactic and/or therapeutic agents). The use of the term "in combination" does not restrict the order in which therapies (e.g., prophylactic and/or therapeutic agents) are administered to a subject with a hyperproliferative cell disorder, especially cancer. A first therapy (e.g., prophylactic and/or therapeutic agent) can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., prophylactic and/or therapeutic agent) to a subject which had, has, or is susceptible to a hyperproliferative cell disorder, especially cancer. The therapies (e.g., prophylactic and/or therapeutic agents) are administered to a subject in a sequence and within a time interval such that the agent of the invention can act together with the other agent to provide an increased benefit than if they were administered otherwise. Any additional therapy (e.g., prophylactic and/or therapeutic agent) can be administered in any order with the other additional therapy (e.g., prophylactic and/or therapeutic agent).

As used herein, the terms "manage", "managing" and "management" refer to the beneficial effects that a subject derives from administration of a therapy (e.g., prophylactic and/or therapeutic agent), which does not result in a cure of the disease. In certain embodiments, a subject is administered one or more therapies (e.g., prophylactic and/or therapeutic agents) to "manage" a disease so as to prevent the progression or worsening of the disease.

As used herein, the term "neoplastic" refers to a disease involving cells that have the potential to metastasize to distal sites. Neoplastic cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. Thus, "non-neoplastic" means that the condition, disease, or disorder does not involve cancer cells.

As used herein, the phrase "non-responsive/refractory" is used to describe patients treated with one or more currently available therapies (e.g., cancer therapies) such as chemotherapy, radiation therapy, surgery, hormonal therapy and/or biological therapy/immunotherapy, particularly a standard therapeutic regimen for the particular cancer, wherein the therapy is not clinically adequate to treat the patients such that these patients need additional effective therapy, e.g., remain unsusceptible to therapy. The phrase can also describe patients who respond to therapy yet suffer from side effects, relapse, develop resistance, etc. In various embodiments, "non-responsive/refractory" means that at least some significant portion of the cancer cells are not killed or their cell division arrested. The determination of whether the cancer cells are "non-responsive/refractory" can be made either in vivo or in vitro by any method known in the art for assaying the effectiveness of treatment on cancer cells, using the art-accepted meanings of "refractory" in such a context. In various embodiments, a cancer is "non-responsive/refractory" where the number of cancer cells has not been significantly reduced, or has increased during the treatment.

As used herein, the terms "prevent," "preventing" and "prevention" refer to the prevention of the onset, recurrence, or spread of a disease in a subject resulting from the administration of a therapy (e.g., prophylactic or therapeutic agent), or a combination of therapies.

As used herein, the term "renal dysfunction" is a disorder of the renal system that detracts from the body's ability to adequately retain essential nutrients and clear out toxic substance from the blood. Renal dysfunction may or may not be associated with a disease.

As used herein, the term "renal disease" is a renal dysfunction that is associated with one or more diseases, such diseases include but are not limited to, chronic renal failure, acute renal failure, myeloma kidney, multiple myeloma, diabetes, cancer, liver disease, benign B-cell hyperproliferation, malignant B-cell hyperproliferation, hypertension, sickle cell anemia, Sjogren's syndrome, lupus, and polycystic kidney disease.

As used herein, the terms "cytoprotective effect on cells", "protection of cells" and "rescuing of cells" mean an inhibition of a pathology-causing cell phenotype or reduction in pathological symptoms of the cells.

As used herein, the terms "an inhibition of a pathology-causing cell phenotype" and "reduction in pathological symptoms" include, but are not limited to, one or more of the following: an increase in cell viability, inhibition of hyperproliferation of cells, activation of NFκB, decrease production of pathologically associated molecules such as TNF-α and IL-6.

As used herein, the term "prophylactic agent" refers to any agent that can be used in the prevention of the onset, recurrence or spread of a disorder associated with renal dysfunction and multiple myeloma, a disorder associated with hyperproliferative cell disease, particularly cancer. In certain embodiments, the term "prophylactic agent" refers to the composition of the present invention. In certain other embodiments, the term "prophylactic agent" refers to a therapy other than the composition of the present invention, e.g., a cancer chemotherapeutic, radiation therapy, hormonal therapy, biological therapy (e.g., immunotherapy). In other embodiments, more than one prophylactic agent may be administered in combination.

As used herein, a "prophylactically effective amount" refers to that amount of a therapy (e.g., a prophylactic agent) sufficient to result in the prevention of the onset, recurrence or spread of a disorder (e.g., a disorder associated with renal disease or a hyperproliferative cell disease, preferably, cancer). A prophylactically effective amount may refer to the amount of therapy (e.g., a prophylactic agent) sufficient to prevent the onset, recurrence or spread of a disorder (e.g., a disorder associated with renal disease or a hyperproliferative cell disease, particularly cancer) in a subject including, but not limited to, subjects predisposed to renal disease or a hyperproliferative cell disease, for example, those genetically predisposed to renal disease, diabetes, infections, or cancer (particularly, myeloma) or previously exposed to carcinogens. A prophylactically effective amount may also refer to the amount of a therapy (e.g., prophylactic agent) that provides a prophylactic benefit in the prevention of a disorder (e.g., a disorder associated with renal disease and a hyperproliferative cell disease). Further, a prophylactically effective amount with respect to a therapy (e.g., prophylactic agent) means that amount of a therapy (e.g., prophylactic agent) alone, or in combination with other therapies (e.g., agents), that provides a prophylactic benefit in the prevention of a disorder (e.g., a disorder associated with renal disease and a hyperproliferative cell disease). Used in connection with an amount of a composition of the present invention, the term can encompass an amount that improves overall prophylaxis or enhances the prophylactic efficacy of or synergies with another therapy (e.g., a prophylactic agent).

A used herein, a "protocol" includes dosing schedules and dosing regimens.

As used herein, the phrase "side effects" encompasses unwanted and adverse effects of a prophylactic or therapeutic agent. Adverse effects are always unwanted, but unwanted effects are not necessarily adverse. An adverse effect from a therapy (e.g., a prophylactic or therapeutic agent) might be harmful or uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art. Many are described in the *Physicians' Desk Reference* (56$^{th}$ ed., 2002, 57$^{th}$ ed., 2003 and 58$^{th}$ ed., 2004).

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human. In a specific embodiment, the subject is a non-human animal. In another embodiment, the subject is a farm animal (e.g., a horse, a pig, a lamb or a cow) or a pet (e.g., a dog, a cat, a rabbit or a bird). In another embodiment, the subject is an animal other than a laboratory animal or animal model (e.g., a mouse, a rat, a guinea pig or a monkey). In a preferred embodiment, the subject is a human. In another preferred embodiment, the subject is a human that has overproduction of proteins in the urine. In a specific embodiment, the proteins are monoclonal protein, paraprotein, M protein, or Bence-Jones proteins. In another preferred embodiment, the subject is a human that has interstitial fibrosis or hyaline casts in the kidney.

As used herein, the terms "treat," "treating" and "treatment" refer to the eradication, reduction or amelioration of a disorder or a symptom thereof, particularly, the eradication, removal, modification, or control of primary, regional, or metastatic cancer tissue that results from the administration of one or more therapies (e.g., therapeutic agents). In certain embodiments, such terms refer to the minimizing or delaying the spread of cancer resulting from the administration of one or more therapies (e.g., therapeutic agents) to a subject with such a disease. In other embodiments, the terms "treat", "treating" and "treatment" refer to the eradication, reduction or amelioration of a disorder or a symptom related to the overproduction of Bence-Jones protein or protecting and/or rescuing renal cells.

As used herein, the term "therapeutic agent" refers to any agent that can be used in the prevention, treatment, or management of a disease (e.g., a disorder associated with renal disease and/or hyperproliferative cell disorder, particularly, myeloma). In certain embodiments, the term "therapeutic agent" refers to a composition of the invention. In certain other embodiments, the term "therapeutic agent" refers to a therapy other than a composition of the present invention such as, e.g., a cancer chemotherapeutic, radiation therapy, hormonal therapy, and/or biological therapy/immunotherapy. In other embodiments, more than one therapy (e.g., a therapeutic agent) may be administered in combination.

As used herein, a "therapeutically effective amount" refers to that amount of a therapy (e.g., a therapeutic agent) sufficient to treat or manage a disorder (e.g., a disorder associated with renal disease, a disorder associated with hyperproliferative cell disease) and, preferably, the amount sufficient to destroy, modify, control or remove primary, regional or metastatic cancer tissue. A therapeutically effective amount may refer to the amount of a therapy (e.g., a therapeutic agent) sufficient to delay or minimize the onset of a disorder (e.g., renal dysfunction or hyperproliferative cell disease), e.g., delay or minimize the spread of cancer. A therapeutically effective amount may also refer to the amount of a therapy (e.g., a therapeutic agent) that provides a therapeutic benefit in the treatment or management of a disorder (e.g., renal dysfunction or myeloma). Further, a therapeutically effective amount with respect to a therapy (e.g., a therapeutic agent) means that amount of a therapy (e.g., therapeutic agent) alone, or in combination with other therapies, that provides a therapeutic benefit in the treatment or management of a disorder (e.g., a hyperproliferative cell disease such as cancer). Used in connection with an amount of a composition of the present invention, the term can encompass an amount that improves overall therapy, reduces or avoids unwanted effects, or enhances the therapeutic efficacy of or synergies with another therapy (e.g., a therapeutic agent).

As used herein, the term "therapy" refers to any protocol, method and/or agent that can be used in the prevention, treatment or management of a disorder (e.g., renal disease, a hyperproliferative cell disorder, a disorder associated with a non-neoplastic hyperproliferative cell disorder) or a symptom thereof. In certain embodiments, the terms "therapies" and "therapy" refer to a biological therapy, supportive therapy, and/or other therapies useful in treatment, management, prevention, or amelioration of a disorder (e.g., renal disease or a hyperproliferative cell disorder and/or a non-neoplastic hyperproliferative cell disorder) or one or more symptoms thereof known to one of skill in the art such as medical personnel.

5. DETAILED DESCRIPTION OF INVENTION

The inventors of the present application have discovered that damage to cultured human renal tubule epithelial cells, induced by light chain (LC) immunoglobulin, can be suppressed dramatically by pituitary adenylate cyclase activating polypeptide that comprises 38 amino acids (PACAP38). Furthermore, it has also been found that PACAP38 directly suppresses growth (i.e., proliferation) of myeloma cells. Thus, PACAP has dual therapeutic effects in the treatment of multiple myeloma: (1) prevention of renal damage and (2) suppression of tumor growth.

Although not intending to be bound by any mechanism of action, the inventors discovered in the present invention that PACAP interacts directly with human renal tubule cells, potentially through $VPAC_2$-R and other receptors, and protects the cells from the light chain-induced damage. The inventors also discovered in the present invention that PACAP suppresses proliferation of multiple myeloma tumor cells.

Accordingly, the present invention relates to methods and compositions that provide for the treatment, management or prevention of any disease with potential damage to renal tubule cells, particularly caused by exposure of the renal tubule cells to excess protein or toxic agents. In particular, when the excess protein activiates NFκB. In specific embodiments, the methods and compositions of the present invention provide treatment, management, or prevention of multiple myeloma and/or renal dysfunction. Specifically, the present invention provides a method for the treatment and prevention of renal cell damage and death, by administering to renal cells or to a mammal in need thereof, an effective amount of a PACAP compound, which includes PACAP and VIP and their agonists, analogs, fragments, or derivatives. In preferred embodiments, the PACAP compound binds to one or more PACAP receptors including $PAC_1$, $VPAC_1$, and/or $VPAC_2$ receptors. In specific embodiments, the present invention provides a method of providing cytoprotective effects to human renal cells. In other embodiments, the present invention provides a method of inhibiting proliferation of human myeloma cells. Further compositions and methods of the invention include other types of therapeutic agents in combination with the composition of the present invention.

The present invention also relates to methods and compositions that provide for the treatment, management or prevention of disorders associated with kidney damage.

The present invention also relates to methods for the treatment, management, and prevention of hyperproliferative cell disorders that have become partially or completely refractory to current treatment.

The present invention provides for the screening and identification of suitable PACAP compounds that comprise one or more PACAP activities, including but not limited to, binding to one or more PACAP receptors and inhibit a pathology-causing cell phenotype.

5.1 Prophylactic/Therapeutic Methods for Renal Dysfunction and Multiple Myeloma In accordance with the methods of the present invention, pharmaceutical compositions comprising PACAP compounds may be used in the treatment, management, and prevention of damage to kidneys and renal cells. In certain embodiments, the method of the present invention can provide treatment, management and prevention of renal dysfunction that involve increase in the level of proteins in the nephritic filtrate. In a specific embodiment, the renal cells are renal tubule epithelial cells. The damage of the cells may be caused by injury or death due to overload of proteins, including but not limited to monoclonal protein, paraprotein, M protein, or Bence-Jones proteins, in certain embodiments, subsequent to proliferation of multiple myeloma cells. The methods of the present invention may also provide treatment, management, and prevention of renal dysfunction caused by, for example, proteins entering the renal tubular system due to impaired glomerular filtration, various toxic agents such as mercury and antibiotics, ischemia/reperfusion injury, trauma, hemorrhage, infections, inflammation, diabetes, cancer, liver disease, enhanced immune reaction including rejection of implanted kidney.

Renal cell injury, including but not limited to tubular, interstitial injury, medullary and papillary defects can be caused by many other proteins and agents as well. Proteinuria is not merely a consequence of glomerular hyperfiltration (an abnormal increase in the filtration rate of the renal glomeruli and a sign of altered glomerular barrier integrity). Abnormal protein trafficking through the glomerular capillary also contributes to progression of renal disease. Brenner B M, et al. *Am J Hypertens*. 14: 335 (1988). Proteins passed by the glomerular filtration mechanism are later reabsorbed by the proximal and distal tubules. However, if the protein concentration of the nephritic filtrate increases, the tubules are eventually injured by the overload of proteins to be cleared, resulting in tubule injury. Furthermore, increased protein concentration in the filtrate may cause proteins to precipitate out of solution and aggregate to form casts within the tubules and clogging them. Protein overload causes increased production of inflammatory mediators such as endothelin-1, monocyte chemoattractant protein 1 (MCP-1), regulated upon activation, normal T cells expressed and secreted (RANTES, a chemotactic cytokine for monocytes and memory T cells and osteopontin). The molecular mechanisms that lead to chemokine overexpression are mediated by NFκB, a transcription factor that promotes gene expression. There is in vitro evidence that albumin and IgG (protein components of human blood) can cause a dose-dependent increase in NFκB activation in proximal tubule cells, an event that is followed by upregulation of RANTES and MCP-1.

In a specific embodiment, the invention provides a method of inhibiting the production of TNF-α in renal cells. In another specific embodiment, the invention provides a method of inhibiting the production of IL6 in renal cells. In another specific embodiment, the invention provides a method of inhibiting the activation of MAP kinase in renal cells. In another embodiment, the invention provides a method of inhibiting NFκB activation in renal cells. In a specific embodiment, the cytoprotective effect on a cell is measured by the level of proinflammatory cytokines produced by the cell. These proinflammatory cytokines include, but are not limited to, TNF-α, IL6, and interferon.

Neither dexamethasone nor PACAP38 suppressed ERK1/2 MAPK activation (FIG. 5) or NFκB p65 activation (FIG. 7) induced by immunoglobulin light chain, but both significantly suppressed NFκB p50 activation (FIG. 6) in renal tubule cells, with approximately the same potency. Although not to be bound by any mechanism, the cytoprotective effect of PACAP38 on renal tubule cells may be mediated by additional mechanisms other than suppression of NFκB activation. It is discovered by the present inventors that both PACAP38 and dexamethasone caused significant suppression of immunoglobulin light chain-induced production of IL6 by renal tubule cells (FIG. 11). Similarly, both PACAP38 and dexamethasone suppressed activation of p38 MAPK (stress-activated protein kinase 2a), a kinase that is thought to be intimately involved in cytokine production (FIG. 12).

In addition, both PACAP38 and dexamethasone suppressed growth of myeloma cells in cultures with approximately the same efficacy, though the mechanisms remain elusive (FIG. 8). However, both proximal tubule cells and human myeloma cells express VPAC$_2$ receptor (FIG. 9), suggesting that the therapeutic effects of PACAP and VIP and their analogs, agonists, fragments, or derivatives, may involve interaction with this receptor (but this does not preclude the possibility that PAC1-R and/or VPAC$_1$-R are involved as well). In conclusion, PACAP38 is a novel, safe, and promising therapeutic agent useful for: protecting the kidney against damage induced by multiple myeloma, suppressing growth of myeloma cells, and protecting the kidney against toxic agents.

Other diseases that may be treated by the methods of the present invention includes those resulting from monoclonal immunoglobulin (Ig) tissue deposition that resulted from malignant or benign monoclonal B cell proliferations. Decourt et al. *Am. J. Path.* 153:313-318 (1998). These diseases are characterized by multivisceral Ig-related material deposits, most often corresponding to monoclonal light chains (LCs) or LC fragments and usually predominating in the kidney. The two most frequent pathological presentations are AL-amyloidosis and nonamyloid (Randall-type) LC deposition disease (LCDD): AL-amyloidosis deposits usually predominate in the glomerular mesangium and in arteriolar walls and mostly involve λ LCs highly organized in β-pleated sheet fibrils. By contrast, LCDD deposits (mostly of the κ type) are amorphous, and predominate along the outer part of basement membranes in the distal tubule and the loop of Henlé, and often associate with marked nodular glomerulosclerosis.

Many substances, including physiological stress, various antibiotic drugs, and toxic agents (e.g., cytocidal agents or cytotoxic agents) may affect renal tubule epithelial cells directly, causing tubule cell injury. Diabetes, liver disease, trauma, hemorrhage, infections can also cause renal dysfunction. A growing body of evidence indicates that inflammatory mechanisms contribute to toxin-induced acute renal failure as well as ischemia/reperfusion injury. Accordingly, the invention provides prevention of renal cell injury, including, but not limited to, tubule cell, tubule epithelial cell, injury that is caused by methods of treatment or antibiotic drugs or toxic substances. In other embodiments, the cells are injured by diabetes, glomerular hyperfiltration and other conditions related to renal dysfunction. Other agents that may cause renal diseases, include but are not limited to, Shiga toxin, Shiga-like toxin, Verotoxin, Shiga toxin-producing *Escherichia coli* (STEC), especially of serotype O157:H7, Ceponis et al. *Mem Inst Oswaldo Cruz, Rio de Janeiro* 100 (Supp. 1): 199-203 (2005), which causes hemolytic uremic syndrome (hemolytic anemic, hemorrhagic colitis, thrombocytopenia) and is the leading cause of acute renal failure in children; diphtheria toxin; abrin; ricin A; pseudomonas exotoxin; cholera toxin; heavy metals, such as, mercury, lead, cisplatin.

In specific embodiments, the present invention also provides methods and compositions for the treatment, management or prevention of the cytotoxic effects of chemotherapy, particularly to protect or rescue renal cells, more preferably, renal tubule cells, from the effects of cytotoxic agents.

5.2 Identification of PACAP Compounds

The invention provides methods of assaying and screening for PACAP compounds, such as PACAP, VIP, their agonists, analogs, fragments, or derivatives, suitable for use in the method of the present invention by incubating agents with cells comprising PACAP receptors, particularly epithelial cells, and then assaying for a reduction in pathology-causing cell phenotype, for example, an increase in cell viability, inhibition of hyperproliferation, and/or decreased amount of pathology-associated molecules (e.g., TNF-α, IL-6) thereby identifying a PACAP compound useful for the method of the invention. Any cell which possesses PAC$_1$, VPAC$_1$, or VPAC$_2$ receptors can be stimulated by PACAP in this manner.

Preferably, the PACAP compound has the general formula:

wherein X is H or a solubility-affecting group such as a C$_{1-20}$ carboxylic acid moiety, such as formyl, acetyl, etc.; a and b are N and C terminal amino acids from the sequence of PACAP38 as shown in FIG. 1, and Y is H, NH$_2$, OH, or C$_{1-4}$ carboxy. For adjustment of lipophilic nature, it is preferred that X is a fatty acid moiety, preferably derived from lauric, myristic, palmitic, stearic, or oleic acid, most preferably from palmitic or stearic acid. Thus expressed, PACAP38 is PACAP$_{[1-38]}$-NH$_2$, i.e., X is H, Y is the NH$_2$ attached to the C-terminal Lysine, and the compound has the complete sequence of 1-38 amino acids of FIG. 1. The polypeptide can be substituted at either end with moieties, which favorably affect the solubility in carrier solution, or which favorably affect the ability of the PACAP compound to resist enzymatic degradation and prolong its biological half-life without substantially adversely affecting the effectiveness of the compound. Thus X can be an organic acid or salt thereof, preferably containing only alkyl groups of C$_{1-25}$, preferably C$_{1-20}$, or a residue from such an acid, e.g., an ether derived from such an acid. Low molecular weight (C$_{1-4}$) acids or acid residues can be used to increase the solubility of the polypeptide in the pharmaceutical composition, or in bodily fluids. Larger molecular weight moieties, such as the C$_{12-20}$ long chain fatty acid residues, can also be used to enhance resistance to enzymatic degradation and prolong biological half-life. Substituents at the C-terminus of the polypeptide can also be used to enhance the solubility of the PACAP compound without deleteriously affecting its usefulness. For example, the amino (NH$_2$) group on the C-terminal amino acid can be substituted by a hydroxyl group or a lower (C$_{1-4}$) alcohol or carboxyl group.

It is also possible to make various substitutions of certain amino acids, contained within the PACAP sequence, to make minor adjustments in the physical properties of the molecule without substantially affecting its usefulness in treatment, management, or prevention of multiple myeloma and/or renal dysfunction. For example, substitution of less reactive amino acids can provide increased stability and shelf life of the pharmaceutical composition. Although other amino acid substitutions are possible, in preferred embodiments, it is possible to make one or more of the following substitutions:

| Location | Substitute (s) |
|---|---|
| For His at position 1 | Tyr, Ala, Arg or Glu |
| For Asp at position 3 | Glu |
| For Gly at position 4 | Ala |
| For Asp at position 8 | Glu |
| For Ser at position 9 | Asn |
| For Ser at position 11 | Thr |
| For Tyr at position 13 | Leu |
| For Met at position 17 | Gly, Ser, Phe, Nle, Arg or Glu |
| For Ala at positions 24, 25 | Ser |

Substitution of D-amino acids can provide increased stability in vivo and prolong the biological half-life. As used in the present application, substitutions will be referred to in brackets prior to the modified PACAP structure. For example, $[Glu^{3,8}]PACAP_{[1-27]}$-$NH_2$ refers to PACAP27 wherein the asparagine at position 3 and the asparagine at position 8 have each been replaced by glutamic acid.

Suitable exemplary compositions are disclosed below.

In a preferred embodiment, the pharmaceutical composition of the present invention comprises PACAP38, its salts, or derivatives. In other preferred embodiments, the pharmaceutical composition of the present invention comprises PACAP27, VIP, their salts, or derivatives. As used herein, "PACAP27" and "PACAP38" refer to the polypeptides which have the same amino acid sequence as amino acids 1-27 and 1-38, respectively, of PACAP38, as shown in FIG. 1. Other suitable PACAP compounds include:

1. $N^\alpha$ Acetyl-$PACAP_{1-38}$-$NH_2$ where $PACAP_{1-38}$ represents amino acids 1-38 of SEQ ID NO:1;
2. $N^\alpha$ Acetyl-$PACAP_{2-38}$-$NH_2$ where $PACAP_{2-38}$ represents amino acids 2-38 of SEQ ID NO:1;
3. $N^\alpha$-Stearyl-$PACAP_{1-38}$-$NH_2$ where $PACAP_{1-38}$ represents amino acids 1-38 of SEQ ID NO:1;
4. $N^\alpha$-Stearyl-$PACAP_{2-38}$-$NH_2$ where $PACAP_{2-38}$ represents amino acids 2-38 of SEQ ID NO:1;
5. $PACAP_{1-38}$-OH where $PACAP_{1-38}$ represents amino $acids_{1-38}$ of SEQ ID NO:1;
6. $PACAP_{1-30}$-$NH_2$ where $PACAP_{1-30}$ represents amino acids 1-30 of SEQ ID NO:1;
7. $PACAP_{2-30}$-$NH_2$ where $PACAP_{2-30}$ represents amino acids 2-30 of SEQ ID NO:1;
8. $N^\alpha$-Acetyl-$PACAP_{2-30}$-$NH_2$ where $PACAP_{2-30}$ represents amino acids 2-30 of SEQ ID NO:1;
9. $PACAP_{1-27}$-$NH_2$ where $PACAP_{1-27}$ represents amino acids 1-27 of SEQ ID NO:1 or SEQ ID NO:2;
10. $N^\alpha$Acetyl-$PACAP_{1-27}$-$NH_2$ where $PACAP_{1-27}$ represents amino acids 1-27 of SEQ ID NO:1 or SEQ ID NO:2;
11. $N^\alpha$-Acetyl-$PACAP_{2-27}$-$NH_2$ where $PACAP_{2-27}$ represents amino acids 2-27 of SEQ ID NO:1 or SEQ ID NO:2;
12. $N^\alpha$-Stearyl-$PACAP_{1-27}$-$NH_2$ where $PACAP_{1-27}$ represents amino acids 1-27 of SEQ ID NO:1 or SEQ ID NO:2;
13. $N^\alpha$-Stearyl-$PACAP_{2-27}$-$NH_2$ where $PACAP_{2-27}$ represents amino acids 2-27 of SEQ ID NO:1 or SEQ ID NO:2;
14. $PACAP_{2-27}$-$NH_2$ where $PACAP_{2-27}$ represents amino acids 2-27 of SEQ ID NO:1 or SEQ ID NO:2;
15. $[Tyr^1]PACAP_{1-b}$-$NH_2$, b=27-38 where $PACAP_{1-b}$ represents amino acids 1-b of SEQ ID NO:1, where b represents amino acids 27 to 38;
16. $[Ala^1]PACAP_{1-b}$-$NH_2$, b=27-38 where $PACAP_{1-b}$ represents amino acids 1-b of SEQ ID NO:1, where b represents amino acids 27 to 38;
17. $[Arg^1]PACAP_{1-b}$-$NH_2$, b=27-38 where $PACAP_{1-b}$ represents amino acids 1-b of SEQ ID NO:1, where b represents amino acids 27 to 38;
18. $[Glu^1]PACAP_{1-b}$-$NH_2$, b=27-38 where $PACAP_{1-b}$ represents amino acids 1-b of SEQ ID NO:1, where b represents amino acids 27 to 38;
19. $[Glu^3]PACAP_{1-b}$-$NH_2$, b=27-38 where $PACAP_{1-b}$ represents amino acids 1-b of SEQ ID NO:1, where b represents amino acids 27 to 38;
20. $[Glu^8]PACAP_{1-b}$-$NH_2$, b=27-38 where $PACAP_{1-b}$ represents amino acids 1-b of SEQ ID NO:1, where b represents amino acids 27 to 38;
21. $[Glu^{3,8}]PACAP_{1-b}$-$NH_2$, b=27-38 where $PACAP_{1-b}$ represents amino acids 1-b of SEQ ID NO:1, where b represents amino acids 27 to 38;
22. $[Asn^9]PACAP_{1-b}$-$NH_2$, b=27-38 where $PACAP_{1-b}$ represents amino acids 1-b of SEQ ID NO:1, where b represents amino acids 27 to 38;
23. $[Thr^{11}]PACAP_{1-b}$-$NH_2$, b=27-38 where $PACAP_{1-b}$ represents amino acids 1-b of SEQ ID NO:1, where b represents amino acids 27 to 38;
24. $[Leu^{13}]PACAP_{1-b}$-$NH_2$, b=27-38 where $PACAP_{1-b}$ represents amino acids 1-b of SEQ ID NO:1, where b represents amino acids 27 to 38;
25. $[Ser^{24,25}]PACAP_{1-b}$-$NH_2$, b=27-38 where $PACAP_{1-b}$ represents a acids 1-b of SEQ ID NO:1, where b represents amino acids 27 to 38;
26. X-$[Gly^{17}]PACAP_{1-b}$-$NH_2$, X=$X_{10-18}$ fatty acid; b=27-38 where $PACAP_{1-b}$ represents amino acids 1-b of SEQ ID NO:1, where b represents amino acids 27 to 38;
27. X-$[Ser^{17}]$PACAP27-$NH_2$, X=$C_{10-18}$ fatty acid;
28. X-$[Phe^{17}]$PACAP27-$NH_2$, X=$C_{10-18}$ fatty acid;
29. X-$[Glu^{17}]$PACAP27-$NH_2$, X=$C_{10-18}$ fatty acid;
30. X-$[Arg^{17}]$PACAP27-$NH_2$, X=$C_{10-18}$ fatty acid;
31. X-$[Nle^{17}]$PACAP27-$NH_2$, X=$C_{10-18}$ fatty acid;
32. X-$[Ala^4]$PACAP(1-23)-$NH_2$, X=$C_{10-18}$ fatty acid;
33. $[Ala^4, Leu^{13}]PACAP_{1-b}$-$NH_2$, b=23-38 where $PACAP_{1-b}$ represents amino acids 1-b of SEQ ID NO:1, where b represents amino acids 23 to 38;
34. $[Leu^{13}]PACAP_{1-b}$-$NH_2$, b=23-38 where $PACAP_{1-b}$ represents amino acids 1-b of SEQ ID NO:1, where b represents amino acids 23 to 38;
35. $[Tyr^1]PACAP_{1-b}$-$NH_2$, b=23-26 where $PACAP_{1-b}$ represents amino acids 1-b of SEQ ID NO:1 or SEQ ID NO:2, where b represents amino acids 23 to 26;
36. $PACAP_{1-b}$-$NH_2$, b=23-26 where $PACAP_{1-b}$ represents amino acids 1-b of SEQ ID NO:1 or SEQ ID NO:2, where b represents amino acids 23 to 26;
37. $PACAP_{1-24}$-$NH_2$ where $PACAP_{1-24}$ represents amino acids 1-24 of SEQ ID NO:1 or SEQ ID NO:2;
38. $PACAP_{1-23}$-OH where $PACAP_{1-23}$ represents amino acids 1-23 of SEQ ID NO:1 or SEQ ID NO:2;
39. $PACAP_{2-23}$-$NH_2$ where $PACAP_{2-23}$ represents amino acids 2-23 of SEQ ID NO:1 or SEQ ID NO:2;
40. $N^\alpha$—X-$PACAP_{1-38}$-$NH_2$, X=$C_{10-18}$ fatty acid where $PACAP_{1-38}$ represents amino acids 1-38 of SEQ ID NO:1;
41. $N^\alpha$—X-$PACAP_{2-38}$-$NH_2$, X=$C_{10-18}$ fatty acid where $PACAP_{2-38}$ represents amino acids 2-38 of SEQ ID NO:1;
42. $N^\alpha$—X-$PACAP_{1-27}$-$NH_2$, X=$C_{10-18}$ fatty acid where $PACAP_{1-27}$ represents amino acids 1-27 of SEQ ID NO:2;

43. N$^\alpha$—X-PACAP$_{2-27}$-NH$_2$, X=C$_{10-18}$ fatty acid where PACAP$_{2-27}$ represents amino acids 2-27 of SEQ ID NO:2;

44. Any peptide or non-peptide agonist (except those listed above) for PAC$_1$ receptor, VPAC$_1$ receptor, or VPAC$_2$ receptor, and organic and inorganic salts thereof.

Further information on uses for PACAP is disclosed in U.S. Pat. No. 6,680,295, the disclosure of which is hereby incorporated by reference.

In preferred embodiments, the PACAP compounds include PACAP, VIP, their agonists, analogs, fragments or derivatives, that bind to one or more PACAP receptors. In preferred embodiments, the composition of the present invention comprises one or more PACAP compounds which include, but are not limited to, peptides comprising amino acid sequences of SEQ ID NO:1, SEQ ID NO:2, SEQ ID NO; 3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27.

In a preferred embodiment, the PACAP compound of the present invention is a fusion protein. In specific embodiment, the heterologous protein is a prophylactic/therapeutic agent. In a specific embodiment, the heterologous protein is interferon.

The invention also encompasses the use of in vivo assays to identify PACAP compound, e.g., by reduction in pathological symptoms, increase in cell viability, inhibition of hyperproliferation, activation of NFκB and/or decreased amount of pathology-associated molecules (e.g., TNF-α, IL-6). These methods are disclosed in Section 6 infra.

In one embodiment, the pathology-causing epithelial cell phenotype is hyperproliferation. Many assays well-known in the art can be used to assess survival and/or growth; for example, cell proliferation can be assayed by measuring ($^3$H)-thymidine incorporation, by direct cell count, by detecting changes in transcription, translation or activity of known genes such as cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as western blotting or immunoprecipitation using commercially available antibodies (for example, many cell cycle marker antibodies are from Santa Cruz Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art.

The present invention provides for cell cycle and cell proliferation analysis by a variety of techniques known in the art, including but not limited to the following: As one example, bromodeoxyuridine (BRDU) incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, *Int. J. Cancer* 38:369; Campana et al., 1988, *J. Immunol. Meth.* 107:79).

Cell proliferation may also be examined using ($^3$H)-thymidine incorporation (see e.g., Chen, 1996, *Oncogene* 13:1395-403; Jeoung, 1995, *J. Biol. Chem.* 270:18367-73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g. Beckman L S 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, *Curr. Biol.* 6:189-99; Vassilev et al., 1995, *J. Cell Sci.* 108:1205-15).

Cell proliferation may be measured by counting samples of a cell population over time (e.g. daily cell counts). Cells may be counted using a hemacytometer and light microscopy (e.g. HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) will exhibit a ploidy value higher than 2N and up to 4N DNA content. Ploidy value and cell-cycle kinetics may be further measured using propidum iodide assay (see e.g. Turner, et al., 1998, *Prostate* 34:175-81). Alternatively, the DNA ploidy may be determined by quantitation of DNA Feulgen staining (which binds to DNA in a stoichiometric manner) on a computerized microdensitometrystaining system (see e.g., Bacus, 1989, *Am. J. Pathol.* 135:783-92). In an another embodiment, DNA content may be analyzed by preparation of a chromosomal spread (Zabalou, 1994, *Hereditas.* 120:127-40; Pardue, 1994, *Meth. Cell Biol.* 44:333-351).

The expression of cell-cycle proteins (e.g., CycA. CycB, CycE, CycD, cdc2, Cdk4/6, Rb, p21, p27, etc.) provide crucial information relating to the proliferative state of a cell or population of cells. For example, identification in an anti-proliferation signaling pathway may be indicated by the induction of p21$^{ciP1}$. Increased levels of p21 expression in cells results in delayed entry into G1 of the cell cycle (Harper et al., 1993, *Cell* 75:805-816; Li et al., 1996, *Curr. Biol.* 6:189-199). p21 induction may be identified by immunostaining using a specific anti-p21 antibody available commercially (e.g. Santa Cruz). Similarly, cell-cycle proteins may be examined by western blot analysis using commercially available antibodies. In another embodiment, cell populations are synchronized prior to detection of a cell cycle protein. Cell cycle proteins may also be detected by FACS (fluorescence-activated cell sorter) analysis using antibodies against the protein of interest.

5.3 Dosages

The present inventors have shown that immunoglobulin light chain-dependent TNF-α production by renal tubule epithelial cells was dose-dependently suppressed by PACAP38 with 10,000 times greater potency than dexamethasone (FIG. 4).

If the magnitude of renal tubule cell injury by LC corresponds to the level of proinflammatory cytokines produced, PACAP may achieve a similar cytoprotective effect in human renal tubule cells with a dose 10,000 times smaller than a comparably effective dose of dexamethasone. Since chronic administration of dexamethasone may cause serious adverse side effects, the use of a much smaller dose of PACAP38 to achieve similar or greater therapeutic effects would be advantageous in terms of its clinical utility. Furthermore, dexamethasone is contraindicated in diabetic patients because they are at increased risk for renal failure and because the steroid can alter blood sugar levels. In contrast, PACAP38 is not expected to suffer these shortcomings.

In specific embodiments, the method comprises administering to a renal cell or a subject, an effective amount of a PACAP compound for providing cytoprotective effect on the renal cell. In specific embodiments, the cytoprotective effect is measured by the level of proinflammatory cytokines produced by the renal cell. In other specific embodiments, the method comprises administering to a myeloma cell or a subject, an effective amount of a PACAP compound for antiproliferation of the myeloma cell. In one embodiment, when the cells that are to be treated are in culture, the effective amount is about $10^{-13}$ M to about $10^{-7}$ M in the culture medium. In another embodiment, when the myeloma cells are in the tissue of a subject, the concentration of the PACAP compound is measured in the interstitial space or blood. In specific embodiments, the effective amount is about $10^{-13}$ M to $10^{-12}$ M, $10^{-12}$ M to $10^{-11}$ M, $10^{-11}$ M to $10^{-10}$ M, $10^{-10}$ M to $10^{-9}$ M, $10^{-9}$ M to $10^{-8}$ M, $10^{-8}$ M to $10^{-7}$ M. In a preferred embodiment, the effective amount is about $10^{-11}$ M. In a most preferred embodiment, the effective amount is about $10^{-9}$ M.

In preferred embodiments, for intravenous administration of the PACAP compound in humans, the concentration of the PACAP compound is 1-2 pmol/kg body weight/minute, 2-4 pmol/kg body weight/minute, 4-6 pmol/kg body weight/minute, 6-8 pmol/kg body weight/minute, 8-10 pmol/kg body weight/minute, 10-12 pmol/kg body weight/minute, 12-14 pmol/kg body weight/minute, 14-16 pmol/kg body weight/minute. In other preferred embodiments, the concentration of the PACAP compound is 4 pmol/kg body weight/minute. The PACAP compound is administered for 30 minutes-1 hour, 1-2 hours, 2-3 hours, 3-4 hours, 4-6 hours, 6-8 hours, 8-10 hours, 10-12 hours, 12-24 hours, or 24-36 hours.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity of the renal disease or hyperproliferative disorder, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56th ed., 2002).

The amount of the composition of the invention which will be effective in the treatment, prevention or management of a renal disease and hyperproliferative cell disorder can be determined by standard research techniques. For example, the dosage of the composition which will be effective in the treatment, prevention or management of renal disease and hyperproliferative cell disorder can be determined by administering the composition to an animal model such as, e.g., the animal models disclosed herein or known to those skilled in the art. In addition, in vitro assays may optionally be employed to help identify optimal dosage ranges.

Selection of the preferred effective dose can be determined (e.g., via clinical trials) by a skilled artisan based upon the consideration of several factors which will be known to one of ordinary skill in the art. Such factors include the disorder to be treated or prevented, the symptoms involved, the patient's body mass, the patient's immune status and other factors known by the skilled artisan to reflect the accuracy of administered pharmaceutical compositions.

In various embodiments, the prophylactic or therapeutic agents are administered less than 5 minutes apart, less than 30 minutes apart, 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

5.4 Patient Population

The invention provides methods for treating, preventing, and managing a renal dysfunction and/or disorder associated with cellular hyperproliferation, particularly of renal epithelial cells, by administrating to a subject in need thereof a therapeutically or prophylactically effective amount of one or more compositions of the invention. In another embodiment, the composition of the invention can be administered in combination with one or more other therapeutic agents. The subject is preferably a mammal such as a non-primate (e.g., cattle, swine, sheep, horses, cats, dogs, rodents, etc.) and a primate (e.g., monkey and a human). In a preferred embodiment, the subject is a human. In specific embodiments, the subject is an infant, a child, or an adult.

The methods and compositions of the invention comprise the administration of one or more compositions of the invention to patients suffering from or expected to suffer from a hyperproliferative cell disorder, e.g., have a genetic predisposition for a hyperproliferative cell disorder or have suffered from a hyperproliferative cell disorder in the past or have been exposed to carcinogen or have been infected or previously exposed to cancer antigens. In a preferred embodiment, the patient is predisposed or is suffering from malignant or benign monoclonal B cell proliferations. In specific embodiments, the patients have pathological presentations of AL-amyloidosis or nonamyloid LC deposition disease. In a preferred embodiment, the kidney of the patient has cast deposits along the tubular membrane basements. In a preferred embodiment, the patient suffers from myeloma kidney. In another preferred embodiment, the patient suffers from diabetes. In other embodiment, the patient suffers from one or more of the following: osteolytic lesions, recurrent bacterial infection, anemia, chronic interstitial nephritis, inflammation, monoclonal gammopathy, Henoch-Schonlein Purpura nephritis (HSPN), lupus nephritis, hemolytic uremic syndrome.

Such patients may or may not have been previously treated for a hyperproliferative cell disorder. The methods and compositions of the invention may be used as a first line or second line treatment. Included in the invention is also the treatment of patients currently undergoing therapies not comprising PACAP compounds to treat a hyperproliferative cell disorder. The methods and compositions of the invention can be used before any adverse effects or intolerance of the non-PACAP based therapies occurs. The invention also encompasses methods for administering one or more compositions of the invention to treat or ameliorate symptoms in refractory patients. The invention also encompasses methods for administering one or more compositions of the invention to prevent the onset or recurrence of a hyperproliferative cell disorder in patients predisposed to having a hyperproliferative cell disorder.

In one embodiment, a patient expected to suffer from a hyperproliferative epithelial cell disorder (e.g., renal epithelial cells) is a patient who has or has had multiple myeloma.

In other embodiments, the invention also provides methods of treatment of hyperproliferative cell disorders as an alternative to current therapies. In one embodiment, the current therapy has proven or may prove too toxic (i.e., results in unacceptable or unbearable side effects) for the patient (e.g., the use of dexamethasone). In another embodiment, the patient has proven refractory to the current therapy. In such embodiments, the invention provides administration of one or more compositions of the invention without any other hyperproliferative cell disorder therapies. In certain embodiments, one or more compositions of the invention can be administered to a patient in need thereof instead of another therapy to treat hyperproliferative cell disorders.

5.5 Other Prophylatic/Therapeutic Agents

In some embodiments, the invention provides methods for treating a patient's renal dysfunction or hyperproliferative cell disorder by administering one or more compositions of the invention in combination with any other therapy for a renal dysfunction or a hyperproliferative cell disorder. Examples of such other therapies include, but are not limited to, anti-inflammatory agents, chemotherapy, radiation therapy, hormonal therapy and/or biological therapy and/or immunotherapy, bone marrow transplantation, gene therapy, dialysis. Treatment for diabetes may also be administered in combination with the composition of the invention. Such treatment includes for example, insulin therapy, such as Humulin, sulfonylureas (glyburide (MICRONASE®, DIABETA®) and glipizide (GLUCOTROL®), metaformin (GLUCOPHAGE®), Troglitazone (REZULIN®), and acarbose (PRECOSE®).

Any anti-inflammatory therapy (e.g., an anti-inflammatory agent) well-known to one of skill in the art can be used in combination with the compositions and methods of the invention. Non-limiting examples of anti-inflammatory agents include non-steroidal anti-inflammatory drugs (NSAIDs), steroidal anti-inflammatory drugs, beta-agonists, anticholingeric agents, antihistamines (e.g., ethanolamines, ethylenediamines, piperazines, and phenothiazine), and methyl xanthines. Examples of NSAIDs include, but are not limited to, aspirin, ibuprofen, salicylates, acetominophen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

In preferred embodiments, one treatment that can be used in combination with the method of the present invention is chemotherapy. In particular embodiments, the treatment includes administration of chemotherapies including, but not limited to thalidomide (THALOMID®), dexamethasone, arsenic trioxide (TRISENOX®), pamidronate, bortezomib (VELCADE®), methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, docetaxel, carmustine, melphalan, cyclophosphamide, lenalidomide (REVLIMID™), etc. Among these patients are patients treated with radiation therapy, hormonal therapy and/or biological therapy/immunotherapy.

Alternatively, the present invention may be used in combination with radiation therapy. In other embodiments, the invention may be used in combination with hormonal therapy and/or biological therapy/immunotherapy. Among these patients are patients treated with chemotherapy and/or radiation therapy. Also among these patients are those who have undergone surgery for the treatment of cancer.

Additionally, the invention also provides methods of treatment of hyperproliferative disease as an alternative to chemotherapy, radiation therapy, hormonal therapy, and/or biological therapy/immunotherapy where the therapy has proven or may prove too toxic, i.e., results in unacceptable or unbearable side effects, for the subject being treated. The subject being treated with the methods of the invention may, optionally, be treated with other cancer treatments such as surgery, chemotherapy, radiation therapy, hormonal therapy or biological therapy, depending on which treatment was found to be unacceptable or unbearable.

In a preferred embodiment, the treatment comprises prednisone, melphalan (Alderan®) in combination with the composition of the present invention.

In another preferred embodiment, the treatment comprises thalidomide in combination with the composition of the present invention.

In another preferred embodiment, the patient is treated with interferon and the composition of the present invention.

5.6 Synthesis of PACAP38, PACAP27, VIP, and Their Related Peptides

PACAP compounds are prepared in a manner which will be apparent to those skilled in the art. The peptides were synthesized by solid phase techniques using an automated peptide synthesizer (Beckman 990B). 4-methyl benzhydrylamine resin and PAM-resin were employed for the synthesis of C-terminal amide form peptides and C-terminal free form peptides, respectively. The peptide chain was elongated on the resin with the use of Na-Boc-amino acid derivatives such as: Boc-Lys(Cl—Z)—OH, Boc-Asn-OH, Boc-Val-OH, Boc-Arg(Tos)-OH, Boc-Gin-OH, Boc-Tyr(Br—Z)—OH, Boc-Leu-OH, Boc-Ala-OH, Boc-Met-OH, Boc-Ser(Bzl)-OH, Boc-Asp(OBzl)-OH, Boc-Thr(Bzl)-OH, Boc-Phe-OH, Boc-Ile-OH, Boc-His(Tos)-OH, Boc-Glu(OBzl)-OH and Boc-Nle-OH.

These $N^\alpha$-Boc amino acid derivatives were successively introduced to the peptide chain in the presence of diisopropylcarbodiimide in dichloromethane with the exception of Boc-Asn-OH and Boc-Glyn-OH, which were coupled in the presence of 1-hydroxybenzotriazole as a catalyst in DMF. The completed, protected peptide resins (90.025 mM each) were treated with 20 mL of anhydrous hydrogen fluoride containing 10% anisole and 100 mg of dithiothreitol for 45 min at 0° C. After removal of the hydrogen fluoride under a stream of nitrogen, the free peptides were precipitated with either ether or ethyl acetate, filtered, and extracted with 2M AcOH. After lyophilization, the crude peptides were obtained. The crude peptides were purified by gel filtration on a column of SEPHADEX G-50 fine (2.5×100 cm) using 2M AcOH containing 0.02% β-mercaptoethanol as an eluent, followed by preparative reverse phase HPLC column (1.5×50 cm) of Vydac C-18 silica (15-20 mm particle size), which was eluted with a linear gradient of 10-35% acetonitrile in 0.1% TFA at a flow rate of 3 mL/min.

The purity of each purified material was confirmed by analytical reverse phase HPLC, amino acid analyses, sequencing and FABMS.

Further information on preparation of the materials referred to in this application is disclosed, for example, in: U.S. Pat. Nos. 5,198,542, 5,128,242; A. Sakiyama et al., *Pep. Chem.* 1991:215 (1991); and C. Kitada et al., *Pep. Chem.* 1990:239 (1991), the disclosures of which are hereby incorporated by reference.

PACAP compounds may be administered intravenously, intraosseously, or subcutaneously to a host in need thereof using a variety of means known to those skilled in the art. It is also possible to administer the polypeptide by a prolonged intravenous (IV) or subcutaneous infusion to attain the optimal concentration of PACAP or VIP for attaining the desired cytoprotective (renal) or cytosuppressive (myeloma cell) effect. Suitable compositions for such administration include an effective amount of the polypeptide in a carrier such as physiological saline, Ringer's solution, glucose (e.g., 3-7%, preferably about 5% by weight), and an isotonic phosphate buffer (pH of about 7). For IV infusion, 0.9% saline containing 0.1% bovine serum albumin may be used. Bovine serum albumin is used for protection of polypeptide from loss due to adsorption. Bovine serum albumin can be replaced by any other inert protein such as human serum albumin and gelatin.

The amount of PACAP compound or VIP compound to be administered sufficient to achieve an effective concentration in the cells to be treated is from about $10^{-13}$ to about $10^{-7}$ M, more preferably from about $10^{-11}$ to about $10^{-7}$ M. The amount of PACAP compound or VIP compound in a pharmaceutical composition for intravenous administration is 10 to 100,000 times the amount that is effective at the active region, preferably 100 to 10,000 times and most preferably 500 to 5,000 times.

5.7 Characterization and Demonstration of Therapeutic or Prophylactic Utility Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-hyperproliferative cell disorder activity of the therapies used in accordance with the present invention also can be determined by using various experimental animal models for the study of anti-hyperproliferative epithelial cell disorders and anti-hyperproliferative endothelial cell disorders.

The renal effects of the therapies used in accordance with the present invention also can be determined by glomerular filtration rate (GFR) and renal blood flow (RBF). Acute renal failure has been associated with reduction in GFR accompanied by a variable decline in RBF.

5.8 Demonstration of Therapeutic Utility

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed, e.g., decreased NFκB activation, rescuing renal epithelial cells, decreased survival/hyperproliferation of B-cells, decreased in the level of Bence-Jones proteins. decreased TNF-α and IL-6 production. A demonstration of any of the aforementioned properties of the contacted cells indicates that the therapeutic agent is effective to treat the condition in the patient. Alternatively, instead of culturing cells from a patient, therapeutic agents and methods may be screened using cells of a epithelial cell line. Many assays standard in the art can be used to assess such survival and/or growth of epithelial cells or B-cells. Further, any assays known to those skilled in the art can be used to evaluate the prophylactic and/or therapeutic utility of the combinatorial therapies disclosed herein for treatment or prevention of a renal disease or a hyperproliferative cell disorder.

5.9 Pharmaceutical Compositions

The compositions of the invention include bulk drug compositions useful in the manufacture of pharmaceutical compositions (e.g., impure or non-sterile compositions) and parenteral pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of one or more PACAP compound useful in the method of the invention and a pharmaceutically acceptable carrier. In a further embodiment, the composition of the invention further comprises an additional therapeutic as discussed supra.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C.1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

As desired, additives such as a dissolution aid (e.g., sodium salicylate, sodium acetate), buffer (e.g., sodium citrate, glycerine), isotonizing agent (e.g., glucose, invert sugar), stabilizer (e.g., human serum albumin, polyethylene glycol), preservatives (e.g., benzyl alcohol, phenol), or analgesics (e.g., benzalkonium chloride, procaine hydrochloride) may be added.

Various delivery systems are known and can be used to administer the PACAP compound or the combination of other prophylactic/therapeutic agents useful for preventing, managing, or treating a renal disease or a hyperproliferative cell disorder, e.g., encapsulation in liposomes, microparticles, microcapsules, recombinant cells capable of expressing the PACAP compound, receptor-mediated endocytosis (see, e.g., Wu and Wu, 1987, *J. Biol. Chem.* 262:4429-4432), construction of a nucleic acid as part of a retroviral or other vector, etc. Methods of administering a prophylactic or therapeutic agent of the invention include, but are not limited to, vaginal, parenteral administration (e.g., intradermal, intramuscular, intraperitoneal, intravenous and subcutaneous), epidural, and mucosal (e.g., intranasal, inhaled, and oral routes). In a specific embodiment, prophylactic or therapeutic agents of the invention are administered intramuscularly, intravenously, intraosseously, or subcutaneously. The prophylactic or therapeutic agents may be administered by any convenient route, for example by infusion or bolus injection, by absorption through epithelial or mucocutaneous linings (e.g., oral mucosa, rectal, topical, including buccal and sublingal, and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

In yet another embodiment, the prophylactic or therapeutic agent can be delivered in a controlled release or sustained release system. In one embodiment, a pump may be used to achieve controlled or sustained release (see Langer, supra; Sefton, 1987, *CRC Crit. Ref Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912, 015; 5,989,463; 5,128,326; International Publication Nos. WO 99/15154 and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526, 938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

Compositions for administration of PACAP include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes and may be prepared by any methods well known in the art of pharmacy. Such methods include the step of bringing into association the ingredients to be administered with the carrier, which constitutes one or more accessory ingredients. In general, the compositions are prepared by uniformly and intimately bringing into association the active ingredients with liquid carriers, liposomes or finely divided solid carriers or both, and then if necessary shaping the product.

Thus, the PACAP compounds of the invention and their physiologically acceptable salts and solvates may be formulated for administration by inhalation or insufflation (either through the mouth or the nose) or oral, parenteral or mucosal (such as buccal, vaginal, rectal, sublingual) administration. In a preferred embodiment, local or systemic parenteral administration is used.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing water. Molded tablets may be made by molding in a suitable machine a mixture of the powdered compound moistened with an inert liquid diluent. The tablets may optionally be coated or scored and may be formulated so as to provide slow or controlled release of the active ingredient therein.

Preparations for oral administration may be suitably formulated to give controlled release of the active compound.

For buccal administration the compositions may take the form of tablets or lozenges formulated in conventional manner.

For administration by inhalation, the prophylactic or therapeutic agents for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The prophylactic or therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The prophylactic or therapeutic agents may also be formulated in rectal compositions such as suppositories or retention enemas, e.g., containing conventional suppository bases such as cocoa butter or other glycerides.

In addition to the formulations described previously, the prophylactic or therapeutic agents may also be formulated as a depot preparation. Such long acting formulations may be administered by implantation (for example subcutaneously or intramuscularly) or by intramuscular injection. Thus, for example, the prophylactic or therapeutic agents may be formulated with suitable polymeric or hydrophobic materials (for example as an emulsion in an acceptable oil) or ion exchange resins, or as sparingly soluble derivatives, for example, as a sparingly soluble salt.

The invention also provides that a prophylactic or therapeutic agent is packaged in a hermetically sealed container such as an ampoule or sachette indicating the quantity. In one embodiment, the prophylactic or therapeutic agent is supplied as a dry sterilized lyophilized powder or water free concentrate in a hermetically sealed container and can be reconstituted, e.g., with water or saline to the appropriate concentration for administration to a subject.

In a preferred embodiment of the invention, the formulation and administration of various chemotherapeutic, biological/immunotherapeutic and hormonal therapeutic agents are known in the art and often described in the *Physician's Desk Reference*, 56$^{th}$ ed. (2002).

In other embodiments of the invention, radiation therapy agents such as radioactive isotopes can be given orally as liquids in capsules or as a drink. Radioactive isotopes can also be formulated for intravenous injections. The skilled oncologist can determine the preferred formulation and route of administration.

In certain embodiments the composition of the invention, are formulated at 1 mg/ml, 5 mg/ml, 10 mg/ml, and 25 mg/ml for intravenous injections and at 5 mg/ml, 10 mg/ml, and 80 mg/ml for repeated subcutaneous administration and intramuscular injection.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

The amount of PACAP in a composition for parenteral administration (e.g., suppository, sublingual tablet, or nasal application) is 100 to 1,000,000 times, the amount that is effective at the active region, preferably 1,000 to 100,000 times and most preferably 5,000 to 50,000 times.

Compositions suitable for topical administration to the skin may be presented as ointments, creams, gels and pastes comprising the compound and a pharmaceutically acceptable carrier. A suitable topical delivery system is a transdermal patch containing the ingredient to be administered.

Sublingual tablets can be prepared by using binders (e.g., hydroxypropylcellulose, hydroxypropylmethylcellulose, or polyethylene glycol), disintegrating agents (e.g., starch or carboxymethylcellulose calcium), and/or lubricants (e.g., magnesium stearate or talc).

Compositions suitable for rectal administration may be presented as a suppository with a suitable base comprising, for example, polyethylene glycol 600, cocoa butter, or a salicylate.

Compositions suitable for nasal administration wherein the carrier is a solid include a coarse powder having a particle size, for example, in the range 20 to 500 microns (µm). Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tables of the kind previously described.

It should be understood that in addition to the ingredients particularly mentioned above, the formulations of this invention may include other agents conventional in the art having regard to the type of formulation in question, for example, those suitable for oral administration may include flavoring agents.

As the PACAP, VIP, their agonists, analogs, fragments, and derivatives, for $PAC_1$, $VPAC_1$, $VPAC_2$ receptor sites are extremely low in toxicity, compositions comprising these compounds are extremely low in toxicity.

5.10 Gene Therapy

In a specific embodiment, nucleic acids that encode a PACAP compound useful for the method of the invention are administered to treat, prevent or manage renal disease or epithelial cell hyperproliferation by way of gene therapy. Gene therapy refers to therapy performed by the administration to a subject of an expressed or expressible nucleic acid. In this embodiment of the invention, the nucleic acids are produce and mediate a prophylactic or therapeutic effect.

Any of the methods for gene therapy available in the art can be used according to the present invention. Exemplary methods are described below. For general reviews of the methods of gene therapy, see Goldspiel et al., 1993, *Clinical Pharmacy* 12:488; Wu and Wu, 1991, *Biotherapy* 3:87; Tolstoshev, 1993, *Ann. Rev. Pharmacol. Toxicol.* 32:573; Mulligan, 1993, *Science* 260:926-932; and Morgan and Anderson, 1993, *Ann. Rev. Biochem.* 62:191; May, 1993, *TIBTECH* 11:155. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a PACAP compound of the invention is encoded by a nucleic acid, the nucleic acid being part of an expression vector that expresses the nucleic acid in a suitable host. In particular, such nucleic acids have promoters, preferably heterologous promoters, the promoter being inducible or constitutive, and, optionally, tissue-specific. In another particular embodiment, the nucleic acid molecules used comprise nucleic acid molecules of the invention flanked by regions that promote homologous recombination at a desired site in the genome, thus providing for intrachromosomal expression of the nucleic acids that encode a PACAP compound useful for the method of the invention (Koller and Smithies, 1989, *PNAS* 86:8932; Zijlstra et al., 1989, *Nature* 342:435).

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy. In a specific embodiment, the nucleic acid sequences are directly administered in vivo. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see e.g., U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide, e.g., through a thioester bond, which is known to enter the cell (e.g., a membrane permeable sequence) and/or nucleus, by administering it in linkage to a ligand subject to receptor-mediated endocytosis (see, e.g., Wu and Wu, 1987, *J. Biol. Chem.* 262:4429) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., International Publication Nos. WO 92/06180; WO 92/22635; WO92/203 16; WO93/14188, WO 93/20221). Alternatively, the nucleic acid can be introduced intracellularly and incorporated within host cell DNA for expression, by homologous recombination (Koller and Smithies, 1989, *PNAS* 86:8932; and Zijlstra et al., 1989, *Nature* 342:435).

In a specific embodiment, a retroviral vector can be used (see Miller et al., 1993, *Meth. Enzymol.* 217:581). These retroviral vectors contain the components necessary for the correct packaging of the viral genome and integration into the host cell DNA. The nucleic acid sequences to be used in gene therapy are cloned into one or more vectors, which facilitates delivery of the nucleic acid into a subject. More detail about retroviral vectors can be found in Boesen et al., 1994, *Biotherapy* 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, *J. Clin. Invest.* 93:644-651; Klein et al., 1994, *Blood* 83:1467-1473; Salmons and Gunzberg, 1993, *Human Gene Therapy* 4:129-141; and Grossman and Wilson, 1993, *Curr. Opin. in Genetics Devel.* 3:110-114.

Adenoviruses are other viral vectors that can be used in gene therapy. Adenoviruses have the advantage of being capable of infecting non-dividing cells. Kozarsky and Wilson, 1993, *Current Opinion in Genetics Development* 3:499 present a review of adenovirus-based gene therapy. Other instances of the use of adenoviruses in gene therapy can be found in Rosenfeld et al., 1991, *Science* 252:431; Rosenfeld et al., 1992, *Cell* 68:143; Mastrangeli et al., 1993, *J. Clin. Invest.* 91:225; International Publication No. WO94/12649; and Wang et al., 1995, *Gene Therapy* 2:775. In a preferred embodiment, adenovirus vectors are used. Adeno-associated virus (AAV) has also been proposed for use in gene therapy (Walsh et al., 1993, *Proc. Soc. Exp. Biol. Med.* 204:289-300; and U.S. Pat. No. 5,436,146).

Numerous techniques are known in the art for the introduction of foreign genes into cells (see, e.g., Loeffler and Behr, 1993, *Meth. Enzymol.* 217:599; Cohen et al., 1993, *Meth. Enzymol.* 217:618) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

6. EXAMPLES

The present invention is further illustrated by the following examples. These examples are provided to aid in the understanding of the invention and are not construed as a limitation thereof.

Example 1

Effect of Immunoglobulin Light Chains on Human Renal Tubule Cells

SV40-immortalized human renal proximal tubule cell cultures were incubated with immunoglobulin light chains (LC) at 50 µM for 3 days (FIG. 2). Proximal tubule cells exposed to LC demonstrated marked morphological changes including cell shrinkage, necrosis, and loss of cell-cell adhesion. PACAP38 alone, at $10^{-9}$ M, did not cause any alteration of cell morphology, but PACAP38 at $10^{-9}$ M prevented the LC-induced changes.

Example 2

Effect of Immunoglobulin Light Chain on TNF-α Production by Human Renal Tubule Cells Without wishing to be bound by theory, the LC-induced injury was hypothesized to be caused by production of proinflammatory cytokines such as interleukin 6 (IL6) and tumor necrosis factor-alpha (TNF-α). Indeed, addition of LC to a final concentration of 50 µM in human renal tubule cell cultures in vitro stimulated the time-dependent production of TNF-α, reaching a maximum level after 48 hours (FIG. 3). TNF-α concentrations were determined by ELISA.

Example 3

Effect of PACAP38, Dexamethasone, and NFκB Inhibitors on Immunoglobulin Light Chain-Induced TNF-α Production by Human Renal Tubule Cells Proinflammatory cytokine production induced by LC was hypothesized to be mediated via activation of an extracellular signal-regulated kinase (ERK)-type mitogen-activated protein kinase (MAPK) and/or nuclear factor kappa B (NFκB). Current treatments for suppression of LC-induced cytokine production include the steroid dexamethasone, and pyrrolidine dithiocarbamate (PDTC), an inhibitor of NFκB. Dexamethasone is also used to suppress myeloma tumor cell growth by stimulating apoptosis.

Varying doses of dexamethasone, PACAP38, MAPK kinase inhibitor (U0126), or PDTC were added to renal tubule cell cultures along with 50 µM LC to determine the effects on LC-induced TNF-α production, as measured by ELISA (FIG. 4). LC-stimulated production of TNF-α was suppressed by both dexamethasone and PACAP38 in a dose-dependent manner. The magnitude of TNF-a suppression by $10^{-9}$ M dexamethasone was comparable to that observed with $10^{-13}$ M PACAP38. Maximal suppression of TNF-α production was achieved by either $10^{-5}$ M dexamethasone or $10^{-9}$ M PACAP38. This demonstrates that in suppressing TNF-α production, PACAP38 is 10,000 times more efficacious than dexamethasone.

In the presence of immunoglobulin light chain (LC), $10^{-9}$ M PACAP38 exhibited dramatic preservation of renal tubule cell survival and morphology (FIG. 2). The same concentration of PACAP38 demonstrated a dramatic suppression of LC-induced production of the cytokine TNF-α (FIG. 4). The suppressive effect of PACAP38 on TNF-α production was 10,000 times greater than that of dexamethasone. This suggests that PACAP38 may require a dose 10,000 times smaller than dexamethasone to achieve in vivo suppression of LC-induced TNF-α production similar to that seen with dexamethasone.

The NFκB inhibitor PDTC was tested at high concentration in this study (0.125 µM and 12.5 µM). At both concentration levels used, PDTC completely suppressed LC-induced TNF-α production. A high dose of the specific MAPK kinase (MEK1/2) inhibitor U0126 also completely suppressed LC-induced TNF-α production. These results support the hypothesis that LC-induced TNF-α production by renal tubule cells involves ERK- and/or NFκB-mediated pathways.

Example 4

Effect of Dexamethasone or PACAP38 on Immunoglobulin Light Chain-Induced Activation of ERK1/2

The ERK-type MAP kinases (ERK1 and ERK2 or, collectively, ERK1/2) are activated by phosphorylation. Evidence of such activation is visualized by antibody detection techniques, using antibody specific for the phosphorylated forms of ERK1/2. As shown in FIG. 4, 50 µM LC induced activation of ERK1/2 in human proximal tubule cells during 3 days incubation. Activation of ERK1/2 appeared to be reduced by co-incubation with either dexamethasone or PACAP38, but the difference was not statistically significant. Thus, the suppressive effects of dexamethasone and PACAP38 on ERK1/2 activation are marginal. ERK1/2 activation was determined by ELISA.

Example 5

Effects of Dexamethasone or PACAP38 on Immunoglobulin Light Chain-Induced Activation of NFκB p50 and p65 Subunits Human renal tubule cells in vitro were incubated with 50 µM LC for 3 days in the presence or absence of dexamethasone or PACAP38, and assayed by ELISA for activation of NFκB subunits (FIGS. 6 & 7). As seen in FIG. 6, incubation with LC produced robust activation of NFκB p50 subunit, which was suppressed significantly by $10^{-7}$ M dexamethasone and by $10^{-9}$ M PACAP38. In contrast, as shown by FIG. 7, incubation with LC failed to produce a dramatic activation of NFκB p65 subunit. Still, activation of the p65 subunit was suppressed relative to controls by $10^{-9}$ M PACAP38. A human Raji cell line (B lymphocyte, Burkitt's lymphoma) was used for positive controls.

Example 6

Suppression of Myeloma Cell Growth by PACAP38

Although the findings above suggest the usefulness of PACAP38 in prevention and treatment of LC-induced renal tubule cell injury in multiple myeloma, it is also important to examine whether or not PACAP38 affects tumor cell growth. A human myeloma cell line (NCI-H929), which produced the lambda (λ) light chains used supra, were grown for 3 days in media containing non-inactivated media, and in the presence or absence of dexamethasone or PACAP38 (FIG. 8). Cell growth was determined by a colorimetric assay that measured the degree of 5-bromo-2-deoxyuridine (BrdU) incorporation by the cells. Addition of either dexamethasone or PACAP38 to the NCI-H929 cultures suppressed cell growth significantly. PACAP38 tended to suppress tumor cell growth at as low a concentration as $10^{-13}$ M, and the maximal suppression was observed at $10^{-7}$ M. At $10^{-9}$ M, dexamethasone demonstrated significant suppression of tumor cell growth, but at $10^{-7}$ M the cells started to grow again. The therapeutic actions of dexamethasone in the treatment of multiple myeloma are attributed to stimulation of apoptosis.

The inventors have shown that PACAP38 suppressed myeloma cell growth in vitro. The myeloma cells were cultured in media containing non-inactivated serum, yet this growth was suppressed by PACAP38 at levels as low as $10^{-11}$ M. At this concentration, no adverse side effects of PACAP are expected in vivo. In vivo, myeloma cells may develop via interactions with various other cells and soluble factors in their microenvironment, especially in the bone marrow. Hideshima T, et al. *Blood*. 101: 703 (2003). Currently, treatment of cancer is shifting from chemotherapy toward modulation of microenvironments. In the bone marrow, PACAP38 suppresses p38 MAPK activation and the production of IL6. Thus, PACAP38 is an ideal antitumor agent for treatment of multiple myeloma because of its beneficial effects on renal tubule cells and its preventive effects on the myeloma cells themselves.

Example 7

Expression of PACAP Receptors in Human Pituitary, Human Renal Tubule Cells and Myeloma Cells PACAP interacts with high affinity with at least three different receptors (PACAP receptors): the PACAP-specific receptor ($PAC_1$-R); and two others ($VPAC_1$-R and $VPAC_2$-R) that can also interact with VIP. Because it is probable that the effects of PACAP are mediated via interaction with one or more of these receptors expressed on the surfaces of cells, applicant examined whether these receptors are expressed in human renal tubule epithelial cells and myeloma cells. Human pituitary was used as a positive control (reference tissue). Total ribonucleic acid (RNA) was extracted and expression of PACAP receptors was determined using reverse transcriptase polymerase chain reaction (RT-PCR) and appropriate receptor-specific primers (FIG. 9). All three PACAP receptors were expressed in pituitary, but neither renal tubule cells nor myeloma cells expressed $PAC_1$-R or $VPAC_1$-R -associated bands at the predicted relative molecular weight. However, a faint band corresponding to $VPAC_2$-R was observed in both renal tubule cells and myeloma cells. Robust bands that did not correspond to either $VPAC_1$-R or $VPAC_2$-R were observed in RNA from renal tubule cells and myeloma cells; the identity of these bands remains unknown.

Example 8

Effect of PACAP on Immunoglobulin Light Chain-Induced IL6 Production in Human Renal Tubule Cells The overproduction of IL6 by neoplastic cells is strongly associated with the growth of multiple myeloma. Kawano M, et al. *Nature*. 332: 83 (1988). Varying doses of PACAP38, dexamethasone, or p38 MAPK kinase inhibitor (SB202190) were added to renal tubule cell cultures along with 50 µM LC to determine the effects on LC-induced IL6 production, as measured by ELISA (FIG. 11). LC-stimulated production of IL6 was suppressed by both dexamethasone and PACAP38 in a dose-dependent manner. The magnitude of IL6 suppression by $10^{-9}$ M PACAP was greater than that observed with either $10^{-9}$ M dexamethasone or 10 µM SB202190.

Example 9

Effect of PACAP on Immunoglobulin Light Chain-Induced p38 MAPK Activation in Human Renal Tubule Cells Cytokine production may depend upon activation (phosphorylation) of p38 MAP kinase (stress-activated protein kinase 2a) isoforms. Evidence of such activation was visualized by ELISA, using antibody specific for phosphorylated p38 MAPK. As shown in FIG. 12, 50 µM LC induced activation of p38 MAPK in human proximal tubule cells during 3 days incubation. Activation of p38 MAPK was reduced significantly, and in a dose-dependent manner, by co-incubation with either dexamethasone or PACAP38. Interestingly, in this assay 10 nM PACAP38 caused reduction of p38 MAPK activation that was comparable to reduction produced by 10 µM SB202190.

Example 10

Animal Model for Immunoglobulin Light Chain-Induced Renal Injury

Male Sprague Dawley rats weighing between 140 and 200 g were used to determine the effects of PACAP on LC-induced renal tubule cell injury in vivo. Animals were anesthetized with Trifluorane in nitrous oxide/oxygen (7:3) during surgery for implanting an intrajugular cannula. After achieving deep anesthesia, animals were shaved over the right clavicular and nuchal regions and the skin cleaned with 70% alcohol. Animals were placed on an operation board and lightly restrained, with the nostrils placed in an inhalation mask through which 1% Trifluorane gas was administered to maintain deep anesthesia during surgery. The skin over the middle portion of the right clavicle was incised, and subcutaneous tissues were cleared to expose the right jugular vein. Two silk surgical sutures (#5) were threaded under and perpendicular to the vein. A small incision was made on the jugular vein, between the two sutures. Polyethylene tubing (PE50), having a stopper on its proximal end and filled with a solution of 0.9% saline and heparin (1000 U/mL), was threaded into the jugular vein through the incision hole so that the distal end of the tubing reached into the right atrium of the heart. Prior to insertion, the tubing was marked at a point 3 cm from its distal end. The distal end of the tubing was inserted through the jugular vein until the mark on the tubing reached the incision point of the jugular vein. The end of the tubing was assumed to have reached into the right atrium of the rat. The tubing was then fixed in place by tightening the two sutures around the vein, and also fixed onto the nearby muscle. The proximal end of the tubing was threaded under the skin toward the nuchal area, where a small incision was made in the skin. The proximal portion of the tubing was pulled out through the incision. The proximal tubing was then introduced through a flexible steel tubing, which was fixed on the nuchal area by means of securing a small end plate attached on the end of steel tubing. The end plate was fixed with the protective jacket for the rat. Each rat was placed in a deep glass jar and the proximal end of the tubing was connected to an infusion pump. During the experiment, the animal in the jar was allowed to move freely and given food and water ad libitum.

Intravenous (intracardiac) infusion via the implanted tubing was made as a rapid infusion, administering 270 mg immunoglobulin light chain protein (LC) per 100 g body weight, over 5 minutes, to attain approximately 100 µM concentration in the body fluid. This dose corresponds to the concentration used in our in vitro experiments with human renal tubule cells, and which caused the cells to undergo considerable deterioration and express various proinflammatory cytokines. Light chain protein was infused continuously by an infusion pump at a rate of 27 mg/hr/100 g body weight, to maintain a concentration of 100 µM LC in the blood. The animals were infused in this manner over 72 hrs with LC alone, or with LC containing varying doses of PACAP38. PACAP38 was given initially as a 10 µg/100 g bolus, followed by slow infusion of PACAP at 0.1 µg to 2 µg per 100 g per hour for 72 hours. At the end of the experiment the animals were deeply anesthetized with Trifluorane, and one kidney was surgically removed for determination of cytokine expression and NFκB activation. Animals were then transcardially perfused with saline (containing heparin), followed by Bouin's fixative. The contralateral kidney was removed and post-fixed in Bouin's solution for later histological examination. In this manner, the effects of PACAP on LC-induced tubule cell injury in vivo were determined.

7. EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

The invention claimed is:

1. A method of treating or managing renal dysfunction caused by multiple myeloma comprising administering to a subject in need thereof a composition comprising an effective amount of one or more PACAP compounds and a pharmaceutically acceptable carrier, wherein the PACAP compounds bind to one or more PACAP receptors or decrease a pathology-causing cell phenotype.

2. The method of claim 1, wherein the PACAP compound is (SEQ ID NO: 1)
His-Ser-Asp-Gly-Ile-Phe-Thr-Asp-Ser-Tyr-Ser-Arg-
Tyr-Arg-Lys-Gln-Met-Ala-Val-Lys-Lys-Tyr-Leu-Ala-
Ala-Val-Leu-Gly-Lys-Arg-Tyr-Lys-Gln-Arg-Val-Lys-
Asn-Lys-NH$_2$, (SEQ ID NO: 2)
His-Ser-Asp-Gly-Ile-Phe-Thr-Asp-Ser-Tyr-Ser-Arg-
Tyr-Arg-Lys-Gln-Met-Ala-Val-Lys-Lys-Tyr-Leu-Ala-
Ala-Val-Leu-NH$_2$, (SEQ ID NO: 3)
His-Ser-Asp-Ala-Val-Phe-Thr-Asp-Asn-Tyr-Thr-Arg-
Leu-Arg-Lys-Gln-Met-Ala-Val-Lys-Lys-Tyr-Leu-Asn-
Ser-Ile-Leu-Asn-NH$_2$, (SEQ ID NO: 4)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-NH$_2$, (SEQ ID NO: 5)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-OH, (SEQ ID NO: 6)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-NH$_2$, (SEQ ID NO: 7)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-OH, (SEQ ID NO: 8)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-NH$_2$, (SEQ ID NO: 9)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-OH, (SEQ ID NO: 10)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-NH$_2$, (SEQ ID NO: 11)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-OH, (SEQ ID NO: 12)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-NH$_2$, (SEQ ID NO: 13)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-OH, (SEQ ID NO: 14)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-NH$_2$, (SEQ ID NO: 15)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-OH, (SEQ ID NO: 16)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-NH$_2$, (SEQ ID NO: 17)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-OH, (SEQ ID NO: 18)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-NH$_2$, (SEQ ID NO: 19)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-OH, (SEQ ID NO: 20)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
NH$_2$, -continued

```
                                       (SEQ ID NO: 21)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
OH, (SEQ ID NO: 22)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-NH2, (SEQ ID NO: 23)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-OH, (SEQ ID NO: 24)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-Asn-NH2, (SEQ ID NO: 25)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-Asn-OH, (SEQ ID NO: 26)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-Asn-Lys-NH2, (SEQ ID NO: 27)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-Asn-Lys-OH,
``` wherein:
X is NHR, where R is H or a solubility affecting group having the acyl group $CH_3(CH_2)_n CO$ where n =0-24; and
Xaa is Met, Gly, Ser, Phe, Nle, Arg or Glu.

3. The method of claim 1, wherein the PACAP compound is at a concentration of $10^{-M}$ to $10^{-7}$ M in the blood of the subject.

4. The method of claim 1, wherein the PACAP compound is administered by intravenous infusion at a rate of 2 pmol/kg body weight/hour to 15 pmol/kg body weight/hour.

5. The method of claim 4, wherein the administration by intravenous infusion is for 2-5 hours.

6. The method of claim 1, wherein the renal dysfunction is caused by ischemia, reperfusion, trauma, hemorrhage, infection, administration of an antibiotic, or exposure to a toxic substance resulting from multiple myeloma or treatment thereof.

7. The method of claim 1, wherein the renal dysfunction is chronic renal failure, acute renal failure, or myeloma kidney.

8. The method of claim 1, wherein the pathology-causing cell phenotype is an increase in cell viability.

9. The method of claim 1, wherein the pathology-causing cell phenotype is an inhibition of hyperproliferation of cells.

10. The method of claim 1, wherein the pathology-causing cell phenotype is a decrease in production of TNF-α and/or IL-6.

11. The method of claim 1, wherein the pathology-causing cell phenotype is an activation of NFκB.

12. A method of treating or managing a hyperproliferative disease caused by multiple myeloma comprising administering to a subject in need thereof a composition comprising an effective amount of one or more PACAP compounds and a pharmaceutically acceptable carrier, wherein the PACAP compounds bind to one or more PACAP receptors or decrease a pathology-causing cell phenotype.

13. The method of claim 12, wherein the PACAP compound is:

```
                                       (SEQ ID NO: 1)
His-Ser-Asp-Gly-Ile-Phe-Thr-Asp-Ser-Tyr-Ser-Arg-
Tyr-Arg-Lys-Gln-Met-Ala-Val-Lys-Lys-Tyr-Leu-Ala-
Ala-Val-Leu-Gly-Lys-Arg-Tyr-Lys-Gln-Arg-Val-Lys-
Asn-Lys-NH2, (SEQ ID NO: 2)
His-Ser-Asp-Gly-Ile-Phe-Thr-Asp-Ser-Tyr-Ser-Arg-
Tyr-Arg-Lys-Gln-Met-Ala-Val-Lys-Lys-Tyr-Leu-Ala-
Ala-Val-Leu-NH2, (SEQ ID NO: 3)
His-Ser-Asp-Ala-Val-Phe-Thr-Asp-Asn-Tyr-Thr-Arg-
Leu-Arg-Lys-Gln-Met-Ala-Val-Lys-Lys-Tyr-Leu-Asn-
Ser-Ile-Leu-Asn-NH2, (SEQ ID NO: 4)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-NH2, (SEQ ID NO: 5)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-OH, (SEQ ID NO: 6)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-NH2, (SEQ ID NO: 7)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-OH, (SEQ ID NO: 8)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-NH2, (SEQ ID NO: 9)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-OH, (SEQ ID NO: 10)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-NH2, (SEQ ID NO: 11)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-OH, (SEQ ID NO: 12)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-NH2, (SEQ ID NO: 13)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-OH, (SEQ ID NO: 14)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-NH2,
```

-continued

```
                                             (SEQ ID NO: 15)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-OH, (SEQ ID NO: 16)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-NH2, (SEQ ID NO: 17)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-OH, (SEQ ID NO: 18)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-NH2, (SEQ ID NO: 19)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-OH, (SEQ ID NO: 20)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
NH2, (SEQ ID NO: 21)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
OH, (SEQ ID NO: 22)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-NH2, (SEQ ID NO: 23)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-OH, (SEQ ID NO: 24)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-Asn-NH2, (SEQ ID NO: 25)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-Asn-OH, (SEQ ID NO: 26)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-Asn-Lys-NH2, (SEQ ID NO: 27)
X-His-Ser-Asp-Gly-Ile-Phe-Thr-Asp-Ser-Tyr-Ser-
Arg-Tyr-Arg-Lys-Gln-Xaa-Ala-Val-Lys-Lys-Tyr-Leu-
Ala-Ala-Val-Leu-Gly-Lys-Arg-Tyr-Lys-Gln-Arg-Val-
Lys-Asn-Lys-OH,
``` wherein:
X is NHR, where R is H or a solubility affecting group having the acyl group $CH_3$ $(CH_2)_n$ CO where n = 0-24; and
Xaa is Met, Gly, Ser, Phe, Nle, Arg or Glu.

14. The method of claim 12, wherein the PACAP compound is at a concentration of $10^{-13}$ M to $10^{-7}$ M in the blood of the subject.

15. The method of claim 12, wherein the PACAP compound is administered by intravenous infusion at a rate of 2 pmol/kg body weight/hour to 15 pmol/kg body weight/hour.

16. The method of claim 15, wherein the administration by intravenous infusion is for 2-5 hours.

17. A method of protecting or rescuing renal tubule cells from damage caused by multiple myeloma comprising administering to a subject in need thereof a composition comprising an effective amount of one or more PACAP compounds and a pharmaceutically acceptable carrier, wherein the PACAP compounds bind to one or more PACAP receptors or decrease a pathology-causing cell phenotype.

18. The method of claim 17, wherein the damage is caused by ischemia, reperfusion, trauma, hemorrhage, exposure to toxic agents or excess proteins resulting from multiple myeloma or treatment thereof.

19. The method of claim 18, wherein the protein is monoclonal protein, paraprotein, M protein or Bence-Jones protein.

20. A method of treating or managing the progression of myeloma comprising administering to a subject in need thereof a composition comprising an effective amount of one or more PACAP compounds and a pharmaceutically acceptable carrier, wherein the PACAP compounds bind to one or more PACAP receptors or decrease a pathology-causing cell phenotype.

21. A method of treating or managing a renal disease caused by the activation of NFκB comprising administering to a subject in need thereof a composition comprising an effective amount of one or more PACAP compounds and a pharmaceutically acceptable carrier, wherein the PACAP compounds bind to one or more PACAP receptors or decrease a pathology-causing cell phenotype.

22. A method of treating or managing a disorder associated with kidney damage caused by multiple myeloma comprising administering to a subject in need thereof a composition comprising an effective amount of one or more PACAP compounds and a pharmaceutically acceptable carrier, wherein the PACAP compounds bind to one or more PACAP receptors or decrease a pathology-causing cell phenotype.

23. The method claim 22, wherein the disorder is hypertension, sickle cell anemia, Sjogren's syndrome, lupus, polycystic kidney disease, chronic renal failure, acute renal failure, diabetes, hemolytic uremic syndrome, lupus nephritis or Henoch-Schonlein purpura nephritis.

24. The method of claim 1, wherein the subject is a human.

25. The method of claim 1, wherein the PACAP compound is administered by a route selected from intravenous, intraperitoneal, intraosseous, subcutaneous, intramuscular, inhalation, intranasal, and oral.

26. The method of claim 1, wherein the PACAP compound is a polypeptide comprising an amino acid sequence having at least 60% sequence identity to SEQ ID NO: 1 or SEQ ID NO: 2.

27. The method of claim 26, wherein the polypeptide comprises an amino acid sequence having at least 80% sequence identity to SEQ ID NO: 1 or SEQ ID NO: 2.

28. The method of claim 27, wherein the polypeptide comprises an amino acid sequence having at least 90% sequence identity to SEQ ID NO: 1 or SEQ ID NO: 2.

29. The method of claim 28, wherein the polypeptide comprises an amino acid sequence having at least 95% sequence identity to SEQ ID NO: 1 or SEQ ID NO: 2.

30. The method of claim 29, wherein the polypeptide comprises an amino acid sequence having at least 99% sequence identity to SEQ ID NO: 1 or SEQ ID NO: 2.

31. The method of claim 30, wherein the polypeptide comprises the amino acid sequence of SEQ ID NO: 1.

32. The method of claim 30, wherein the polypeptide comprises the amino acid sequence of SEQ ID NO: 2.

\* \* \* \* \*